US006825178B1

(12) United States Patent
Pier

(10) Patent No.: US 6,825,178 B1
(45) Date of Patent: Nov. 30, 2004

(54) METHODS AND PRODUCTS FOR TREATING PSEUDOMONAS INFECTION

(75) Inventor: Gerald B. Pier, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/405,735

(22) Filed: Sep. 24, 1999

Related U.S. Application Data

(62) Division of application No. 08/681,838, filed on Jul. 29, 1996, now Pat. No. 6,245,735.
(51) Int. Cl.$^7$ .................. A01N 43/04; A01N 37/18; A61K 38/00; C07K 1/00; C07H 21/02
(52) U.S. Cl. .................. 514/54; 514/2; 514/14; 514/23; 530/402; 435/6; 435/7.1; 536/22.1; 536/123.1
(58) Field of Search .................. 435/6, 7.1; 536/22.1, 536/123.1; 514/2, 23, 14, 54; 530/402

(56) References Cited

U.S. PATENT DOCUMENTS

| 5,240,846 A | 8/1993 | Collins et al. .............. 435/240 |
| 5,407,796 A | 4/1995 | Cutting et al. .............. 435/6 |
| 5,434,086 A | 7/1995 | Collins et al. .............. 436/125 |

FOREIGN PATENT DOCUMENTS

| WO | WO91/02796 | 3/1991 |
| WO | WO93/12240 | 6/1993 |
| WO | WO93/17040 | 9/1993 |
| WO | WO93/24641 | 12/1993 |
| WO | WO94/04669 | 3/1994 |
| WO | WO94/04671 | 3/1994 |
| WO | WO94/25607 | 11/1994 |
| WO | WO95/06743 | 3/1995 |
| WO | WO95/13365 | 5/1995 |
| WO | WO95/25796 | 9/1995 |
| WO | WO95/28494 | 10/1995 |

OTHER PUBLICATIONS

Pennington et al J. of Inf Dis vol. 144 (0) pp 599–603 1981.*
Pier, G.B., et al., "Role of Mutant CFTR in Hypersusceptibility of Cystic Fibrosis Patients to Lung Infections", *Science*, 1996, 271:64–67.
Masoud, H., et al., "Structural Elucidation of the Lipopolysaccharide Core Region of the O–Chain–Deficient Mutant Strain A28 From *Pseudomonas aeruginosa* Serotype 06 (International Antigenic Typing Scheme)", *Journal of Bacteriology*, 1995, 177:23:6718–6726.
Imundo, L., et al., "Cystic Fibrosis Epithellial Cells Have a Receptor for Pathogenic Bacteria on Their Apical Surface", *Proc. Natl. Acad.,* 1995, 92:3019–3023.

Zar, H., et al., "Binding of Pseudomonas Aeruginosa to Respiratory Epithelial Cells From Patients With Various Mutations in the Cystic Fibrosis Transmembrane Regulator" *The Journal of Pediatrics*, 1995, 126:2:230–233.
Masoud, H., et al., "General Strategy for Structural Analysis of the Oligosaccharide Region of Region of Lipooligosaccharides. Structure of the Oligosaccharide Component of *Pseudomonas aeruginosa* IATS Serotype 06 Mutant R5 Rough–Type Lipopolysaccharide", *Biochemistry*, 1994, 33:10568–10578.
DeKievit, T.R., et al.,"Monoclonal Antibodies That Distinguish Inner Core, Outer Core, and Lipid a Regions of *Pseudomnas aeruginosa* Lipopolysaccharide", *Journal of Bacteriology*, 1994, (Dec.) 7129–7139.
Boucher, R.C., et al., "Clinical Protocol–Gene Therapy For Cystic Fibrosis Using Ei–Deleted Adenovirus:A Phase I Trial in the Nasel Cavity", *Human Gene Therapy*, 1994, 5:615–639.
Middleton, P.G., et al., "Nasal Application of the Cationic Liposome DC–Chol:Dope Does Not Alter Ion Transport, Lung Function or Bacterial Growth", *Eur Respir J.,* 1994, 7:442–445.
Riordan, J.R. et al., "Identification of the Cystic Fibrosis Gene: Cloning and Character–_ization of Complimentary DNA", *Genbank*, Dec. 15, 1989, Acession No. M28668.
Rowe, Peter S., et al., "Structure of the Core Oligosaccharide from the Lipopolysaccharide of *Pseudomonas aeruginosa* PAC1R and its Defective Mutants", *Eur. J. Biochem* 1983, 132:329–337.
Kropinski, A.M., "The Extraction and Analysis of Lipopolysaccharides From *Pseudomonas aeruginosa* Strain PAO, and Three Rough Mutants", *National Research Council of Canada*, 1979, 25:390–398.
Riordan, J., et al., "Identification of the Cystic Fibrosis Gene: Cloning and Characterization of Complementary DNA", *Science*, 1989, 245:1066–1072.

(List continued on next page.)

Primary Examiner—Jeffrey Siew
(74) Attorney, Agent, or Firm—Wolf,Greenfield & Sacks,PC

(57) ABSTRACT

Methods and products for upregulating cystic fibrosis transmembrane conductance regulators are provided, including methods and products for the treatment of *P. aeruginosa* infection. The products include polysaccharides that interact with the cystic fibrosis transmembrane conductance regulator (CFTR). The polysaccharide compositions of the invention may be administered to a subject in order to enhance the uptake of *P. aeruginosa* into the epithelial cells of the subject. The invention also encompasses compositions comprising a lipopolysaccharide-binding region of a CFTR linked to an anti-Pseudomal drug and methods of use of such compositions. Compositions and methods for gene therapy are also disclosed. The compositions include polysaccharides that bind to CFTR coupled to a gene delivery vehicle.

28 Claims, No Drawings

OTHER PUBLICATIONS

Zar H., et al., "Binding of *Pseudomonas aeruginosa* to Respiratory Epithelial Cells From Patients With Various Mutations in the Cystic Fibrosis Transmembrane Regulator", *J Pediatrics,* 1989, 126:2:230–2331.

Pier, G., et al., "Cycstic Fibrosis Transmembrane Conductance Regulator is an Epithelial Cell Receptor for Clearance of *Pseudomonas aeruginosa* From the Lung", *Proc Nat. Acad. Sci.,* 1997, 94:12088–93.

Pier, G., et al., "Salmonella Typhi Uses CFTR to Enter Intestinal Epithelial Cells", *Nature,* 1998, 392:79–82.

Pier, G., et al., Cystic Fibrosis Trnasmembrane Conductance Regulator–Mediated Corneal Epithelial Cell Ingestion of *Pseudomonas aeruginosa* is a Key Component in the Pathogenesis of Experimental Murine Keratitis, *Infect Immun.,* 1999, 67:1481–92.

* cited by examiner

SEQUENCE LISTING

```
<160> NUMBER OF SEQ ID NOS:  4

<210> SEQ ID NO 1
<211> LENGTH: 6129
<212> TYPE: DNA
<213> ORGANISM: Homo Sapiens
<220> FEATURE:
<221> NAME/KEY: CDS
<222> LOCATION: (133)...(4575)

<400> SEQUENCE: 1
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga cc atg cag agg tcg cct ctg gaa aag gcc agc gtt gtc tcc     171
               Met Gln Arg Ser Pro Leu Glu Lys Ala Ser Val Val Ser
                 1               5                  10 aaa ctt ttt ttc agc tgg acc aga cca att ttg agg aaa gga tac aga       219
Lys Leu Phe Phe Ser Trp Thr Arg Pro Ile Leu Arg Lys Gly Tyr Arg
     15                  20                  25 cag cgc ctg gaa ttg tca gac ata tac caa atc cct tct gtt gat tct       267
```

|                                                                                     |      |
|-------------------------------------------------------------------------------------|------|
| Gln Arg Leu Glu Leu Ser Asp Ile Tyr Gln Ile Pro Ser Val Asp Ser<br>30          35               40              45 |      |
| gct gac aat cta tct gaa aaa ttg gaa aga gaa tgg gat aga gag ctg<br>Ala Asp Asn Leu Ser Glu Lys Leu Glu Arg Glu Trp Asp Arg Glu Leu<br>         50              55              60 | 315  |
| gct tca aag aaa aat cct aaa ctc att aat gcc ctt cgg cga tgt ttt<br>Ala Ser Lys Lys Asn Pro Lys Leu Ile Asn Ala Leu Arg Arg Cys Phe<br>     65              70              75 | 363  |
| ttc tgg aga ttt atg ttc tat gga atc ttt tta tat tta ggg gaa gtc<br>Phe Trp Arg Phe Met Phe Tyr Gly Ile Phe Leu Tyr Leu Gly Glu Val<br> 80              85              90 | 411  |
| acc aaa gca gta cag cct ctc tta ctg gga aga atc ata gct tcc tat<br>Thr Lys Ala Val Gln Pro Leu Leu Leu Gly Arg Ile Ile Ala Ser Tyr<br>95              100             105 | 459  |
| gac ccg gat aac aag gag gaa cgc tct atc gcg att tat cta ggc ata<br>Asp Pro Asp Asn Lys Glu Glu Arg Ser Ile Ala Ile Tyr Leu Gly Ile<br>110         115             120             125 | 507  |
| ggc tta tgc ctt ctc ttt att gtg agg aca ctg ctc cta cac cca gcc<br>Gly Leu Cys Leu Leu Phe Ile Val Arg Thr Leu Leu Leu His Pro Ala<br>        130             135             140 | 555  |
| att ttt ggc ctt cat cac att gga atg cag atg aga ata gct atg ttt<br>Ile Phe Gly Leu His His Ile Gly Met Gln Met Arg Ile Ala Met Phe<br>    145             150             155 | 603  |
| agt ttg att tat aag aag act tta aag ctg tca agc cgt gtt cta gat<br>Ser Leu Ile Tyr Lys Lys Thr Leu Lys Leu Ser Ser Arg Val Leu Asp<br>160             165             170 | 651  |
| aaa ata agt att gga caa ctt gtt agt ctc ctt tcc aac aac ctg aac<br>Lys Ile Ser Ile Gly Gln Leu Val Ser Leu Leu Ser Asn Asn Leu Asn<br>175             180             185 | 699  |
| aaa ttt gat gaa gga ctt gca ttg gca cat ttc gtg tgg atc gct cct<br>Lys Phe Asp Glu Gly Leu Ala Leu Ala His Phe Val Trp Ile Ala Pro<br>190             195             200             205 | 747  |
| ttg caa gtg gca ctc ctc atg ggg cta atc tgg gag ttg tta cag gcg<br>Leu Gln Val Ala Leu Leu Met Gly Leu Ile Trp Glu Leu Leu Gln Ala<br>        210             215             220 | 795  |
| tct gcc ttc tgt gga ctt ggt ttc ctg ata gtc ctt gcc ctt ttt cag<br>Ser Ala Phe Cys Gly Leu Gly Phe Leu Ile Val Leu Ala Leu Phe Gln<br>    225             230             235 | 843  |
| gct ggg cta ggg aga atg atg atg aag tac aga gat cag aga gct ggg<br>Ala Gly Leu Gly Arg Met Met Met Lys Tyr Arg Asp Gln Arg Ala Gly<br>240             245             250 | 891  |
| aag atc agt gaa aga ctt gtg att acc tca gaa atg att gaa aat atc<br>Lys Ile Ser Glu Arg Leu Val Ile Thr Ser Glu Met Ile Glu Asn Ile<br>255             260             265 | 939  |
| caa tct gtt aag gca tac tgc tgg gaa gaa gca atg gaa aaa atg att<br>Gln Ser Val Lys Ala Tyr Cys Trp Glu Glu Ala Met Glu Lys Met Ile<br>270             275             280             285 | 987  |
| gaa aac tta aga caa aca gaa ctg aaa ctg act cgg aag gca gcc tat<br>Glu Asn Leu Arg Gln Thr Glu Leu Lys Leu Thr Arg Lys Ala Ala Tyr<br>        290             295             300 | 1035 |
| gtg aga tac ttc aat agc tca gcc ttc ttc tca ggg ttc ttt gtg<br>Val Arg Tyr Phe Asn Ser Ser Ala Phe Phe Ser Gly Phe Phe Val<br>    305             310             315 | 1083 |
| gtg ttt tta tct gtg ctt ccc tat gca cta atc aaa gga atc atc ctc<br>Val Phe Leu Ser Val Leu Pro Tyr Ala Leu Ile Lys Gly Ile Ile Leu<br>320             325             330 | 1131 |
| cgg aaa ata ttc acc acc atc tca ttc tgc att gtt ctg cgc atg gcg<br>Arg Lys Ile Phe Thr Thr Ile Ser Phe Cys Ile Val Leu Arg Met Ala<br>335             340             345 | 1179 |

-continued

| | |
|---|---|
| gtc act cgg caa ttt ccc tgg gct gta caa aca tgg tat gac tct ctt<br>Val Thr Arg Gln Phe Pro Trp Ala Val Gln Thr Trp Tyr Asp Ser Leu<br>350                        355                        360                        365 | 1227 |
| gga gca ata aac aaa ata cag gat ttc tta caa aag caa gaa tat aag<br>Gly Ala Ile Asn Lys Ile Gln Asp Phe Leu Gln Lys Gln Glu Tyr Lys<br>                        370                        375                        380 | 1275 |
| aca ttg gaa tat aac tta acg act aca gaa gta gtg atg gag aat gta<br>Thr Leu Glu Tyr Asn Leu Thr Thr Thr Glu Val Val Met Glu Asn Val<br>               385                             390                        395 | 1323 |
| aca gcc ttc tgg gag gag gga ttt ggg gaa tta ttt gag aaa gca aaa<br>Thr Ala Phe Trp Glu Glu Gly Phe Gly Glu Leu Phe Glu Lys Ala Lys<br>             400                        405                        410 | 1371 |
| caa aac aat aac aat aga aaa act tct aat ggt gat gac agc ctc ttc<br>Gln Asn Asn Asn Asn Arg Lys Thr Ser Asn Gly Asp Asp Ser Leu Phe<br>         415                        420                        425 | 1419 |
| ttc agt aat ttc tca ctt ctt ggt act cct gtc ctg aaa gat att aat<br>Phe Ser Asn Phe Ser Leu Leu Gly Thr Pro Val Leu Lys Asp Ile Asn<br>430                        435                        440                        445 | 1467 |
| ttc aag ata gaa aga gga cag ttg ttg gcg gtt gct gga tcc act gga<br>Phe Lys Ile Glu Arg Gly Gln Leu Leu Ala Val Ala Gly Ser Thr Gly<br>                        450                        455                        460 | 1515 |
| gca ggc aag act tca ctt cta atg atg att atg gga gaa ctg gag cct<br>Ala Gly Lys Thr Ser Leu Leu Met Met Ile Met Gly Glu Leu Glu Pro<br>               465                             470                        475 | 1563 |
| tca gag ggt aaa att aag cac agt gga aga att tca ttc tgt tct cag<br>Ser Glu Gly Lys Ile Lys His Ser Gly Arg Ile Ser Phe Cys Ser Gln<br>             480                        485                        490 | 1611 |
| ttt tcc tgg att atg cct ggc acc att aaa gaa aat atc atc ttt ggt<br>Phe Ser Trp Ile Met Pro Gly Thr Ile Lys Glu Asn Ile Ile Phe Gly<br>         495                        500                        505 | 1659 |
| gtt tcc tat gat gaa tat aga tac aga agc gtc atc aaa gca tgc caa<br>Val Ser Tyr Asp Glu Tyr Arg Tyr Arg Ser Val Ile Lys Ala Cys Gln<br>510                        515                        520                        525 | 1707 |
| cta gaa gag gac atc tcc aag ttt gca gag aaa gac aat ata gtt ctt<br>Leu Glu Glu Asp Ile Ser Lys Phe Ala Glu Lys Asp Asn Ile Val Leu<br>                        530                        535                        540 | 1755 |
| gga gaa ggt gga atc aca ctg agt gga ggt caa cga gca aga att tct<br>Gly Glu Gly Gly Ile Thr Leu Ser Gly Gly Gln Arg Ala Arg Ile Ser<br>                        545                        550                        555 | 1803 |
| tta gca aga gca gta tac aaa gat gct gat ttg tat tta tta gac tct<br>Leu Ala Arg Ala Val Tyr Lys Asp Ala Asp Leu Tyr Leu Leu Asp Ser<br>         560                        565                        570 | 1851 |
| cct ttt gga tac cta gat gtt tta aca gaa aaa gaa ata ttt gaa agc<br>Pro Phe Gly Tyr Leu Asp Val Leu Thr Glu Lys Glu Ile Phe Glu Ser<br>575                        580                        585 | 1899 |
| tgt gtc tgt aaa ctg atg gct aac aaa act agg att ttg gtc act tct<br>Cys Val Cys Lys Leu Met Ala Asn Lys Thr Arg Ile Leu Val Thr Ser<br>590                        595                        600                        605 | 1947 |
| aaa atg gaa cat tta aag aaa gct gac aaa ata tta att ttg aat gaa<br>Lys Met Glu His Leu Lys Lys Ala Asp Lys Ile Leu Ile Leu Asn Glu<br>                        610                        615                        620 | 1995 |
| ggt agc agc tat ttt tat ggg aca ttt tca gaa ctc caa aat cta cag<br>Gly Ser Ser Tyr Phe Tyr Gly Thr Phe Ser Glu Leu Gln Asn Leu Gln<br>                        625                        630                        635 | 2043 |
| cca gac ttt agc tca aaa ctc atg gga tgt gat tct ttc gac caa ttt<br>Pro Asp Phe Ser Ser Lys Leu Met Gly Cys Asp Ser Phe Asp Gln Phe<br>             640                        645                        650 | 2091 |
| agt gca gaa aga aga aat tca atc cta act gag acc tta cac cgt ttc<br>Ser Ala Glu Arg Arg Asn Ser Ile Leu Thr Glu Thr Leu His Arg Phe<br>         655                        660                        665 | 2139 |

-continued

```
tca tta gaa gga gat gct cct gtc tcc tgg aca gaa aca aaa aaa caa    2187
Ser Leu Glu Gly Asp Ala Pro Val Ser Trp Thr Glu Thr Lys Lys Gln
670                 675                 680                 685 tct ttt aaa cag act gga gag ttt ggg gaa aaa agg aag aat tct att    2235
Ser Phe Lys Gln Thr Gly Glu Phe Gly Glu Lys Arg Lys Asn Ser Ile
            690                 695                 700 ctc aat cca atc aac tct ata cga aaa ttt tcc att gtg caa aag act    2283
Leu Asn Pro Ile Asn Ser Ile Arg Lys Phe Ser Ile Val Gln Lys Thr
        705                 710                 715 ccc tta caa atg aat ggc atc gaa gag gat tct gat gag cct tta gag    2331
Pro Leu Gln Met Asn Gly Ile Glu Glu Asp Ser Asp Glu Pro Leu Glu
    720                 725                 730 aga agg ctg tcc tta gta cca gat tct gag cag gga gag gcg ata ctg    2379
Arg Arg Leu Ser Leu Val Pro Asp Ser Glu Gln Gly Glu Ala Ile Leu
735                 740                 745 cct cgc atc agc gtg atc agc act ggc ccc acg ctt cag gca cga agg    2427
Pro Arg Ile Ser Val Ile Ser Thr Gly Pro Thr Leu Gln Ala Arg Arg
750                 755                 760                 765 agg cag tct gtc ctg aac ctg atg aca cac tca gtt aac caa ggt cag    2475
Arg Gln Ser Val Leu Asn Leu Met Thr His Ser Val Asn Gln Gly Gln
            770                 775                 780 aac att cac cga aag aca aca gca tcc aca cga aaa gtg tca ctg gcc    2523
Asn Ile His Arg Lys Thr Thr Ala Ser Thr Arg Lys Val Ser Leu Ala
        785                 790                 795 cct cag gca aac ttg act gaa ctg gat ata tat tca aga agg tta tct    2571
Pro Gln Ala Asn Leu Thr Glu Leu Asp Ile Tyr Ser Arg Arg Leu Ser
    800                 805                 810 caa gaa act ggc ttg gaa ata agt gaa gaa att aac gaa gaa gac tta    2619
Gln Glu Thr Gly Leu Glu Ile Ser Glu Glu Ile Asn Glu Glu Asp Leu
815                 820                 825 aag gag tgc ctt ttt gat gat atg gag agc ata cca gca gtg act aca    2667
Lys Glu Cys Leu Phe Asp Asp Met Glu Ser Ile Pro Ala Val Thr Thr
830                 835                 840                 845 tgg aac aca tac ctt cga tat att act gtc cac aag agc tta att ttt    2715
Trp Asn Thr Tyr Leu Arg Tyr Ile Thr Val His Lys Ser Leu Ile Phe
            850                 855                 860 gtg cta att tgg tgc tta gta att ttt ctg gca gag gtg gct gct tct    2763
Val Leu Ile Trp Cys Leu Val Ile Phe Leu Ala Glu Val Ala Ala Ser
        865                 870                 875 ttg gtt gtg ctg tgg ctc ctt gga aac act cct ctt caa gac aaa ggg    2811
Leu Val Val Leu Trp Leu Leu Gly Asn Thr Pro Leu Gln Asp Lys Gly
    880                 885                 890 aat agt act cat agt aga aat aac agc tat gca gtg att atc acc agc    2859
Asn Ser Thr His Ser Arg Asn Asn Ser Tyr Ala Val Ile Ile Thr Ser
895                 900                 905 acc agt tcg tat tat gtg ttt tac att tac gtg gga gta gcc gac act    2907
Thr Ser Ser Tyr Tyr Val Phe Tyr Ile Tyr Val Gly Val Ala Asp Thr
910                 915                 920                 925 ttg ctt gct atg gga ttc ttc aga ggt cta cca ctg gtg cat act cta    2955
Leu Leu Ala Met Gly Phe Phe Arg Gly Leu Pro Leu Val His Thr Leu
            930                 935                 940 atc aca gtg tcg aaa att tta cac cac aaa atg tta cat tct gtt ctt    3003
Ile Thr Val Ser Lys Ile Leu His His Lys Met Leu His Ser Val Leu
        945                 950                 955 caa gca cct atg tca acc ctc aac acg tta aaa gca ggt ggg att ctt    3051
Gln Ala Pro Met Ser Thr Leu Asn Thr Leu Lys Ala Gly Gly Ile Leu
    960                 965                 970 aat aga ttc tcc aaa gat ata gca att ttg gat gac ctt ctg cct ctt    3099
Asn Arg Phe Ser Lys Asp Ile Ala Ile Leu Asp Asp Leu Leu Pro Leu
```

```
                                                               -continued 975            980            985
acc ata ttt gac ttc atc cag ttg tta tta att gtg att gga gct ata        3147
Thr Ile Phe Asp Phe Ile Gln Leu Leu Leu Ile Val Ile Gly Ala Ile
990             995            1000           1005 gca gtt gtc gca gtt tta caa ccc tac atc ttt gtt gca aca gtg cca        3195
Ala Val Val Ala Val Leu Gln Pro Tyr Ile Phe Val Ala Thr Val Pro
        1010           1015           1020 gtg ata gtg gct ttt att atg ttg aga gca tat ttc ctc caa acc tca        3243
Val Ile Val Ala Phe Ile Met Leu Arg Ala Tyr Phe Leu Gln Thr Ser
    1025           1030           1035 cag caa ctc aaa caa ctg gaa tct gaa ggc agg agt cca att ttc act        3291
Gln Gln Leu Lys Gln Leu Glu Ser Glu Gly Arg Ser Pro Ile Phe Thr
1040           1045           1050 cat ctt gtt aca agc tta aaa gga cta tgg aca ctt cgt gcc ttc gga        3339
His Leu Val Thr Ser Leu Lys Gly Leu Trp Thr Leu Arg Ala Phe Gly
        1055           1060           1065 cgg cag cct tac ttt gaa act ctg ttc cac aaa gct ctg aat tta cat        3387
Arg Gln Pro Tyr Phe Glu Thr Leu Phe His Lys Ala Leu Asn Leu His
1070           1075           1080           1085 act gcc aac tgg ttc ttg tac ctg tca aca ctg cgc tgg ttc caa atg        3435
Thr Ala Asn Trp Phe Leu Tyr Leu Ser Thr Leu Arg Trp Phe Gln Met
        1090           1095           1100 aga ata gaa atg att ttt gtc atc ttc ttc att gct gtt acc ttc att        3483
Arg Ile Glu Met Ile Phe Val Ile Phe Phe Ile Ala Val Thr Phe Ile
    1105           1110           1115 tcc att tta aca aca gga gaa gga gaa gga aga gtt ggt att atc ctg        3531
Ser Ile Leu Thr Thr Gly Glu Gly Glu Gly Arg Val Gly Ile Ile Leu
        1120           1125           1130 act tta gcc atg aat atc atg agt aca ttg cag tgg gct gta aac tcc        3579
Thr Leu Ala Met Asn Ile Met Ser Thr Leu Gln Trp Ala Val Asn Ser
    1135           1140           1145 agc ata gat gtg gat agc ttg atg cga tct gtg agc cga gtc ttt aag        3627
Ser Ile Asp Val Asp Ser Leu Met Arg Ser Val Ser Arg Val Phe Lys
1150           1155           1160           1165 ttc att gac atg cca aca gaa ggt aaa cct acc aag tca acc aaa cca        3675
Phe Ile Asp Met Pro Thr Glu Gly Lys Pro Thr Lys Ser Thr Lys Pro
        1170           1175           1180 tac aag aat ggc caa ctc tcg aaa gtt atg att att gag aat tca cac        3723
Tyr Lys Asn Gly Gln Leu Ser Lys Val Met Ile Ile Glu Asn Ser His
    1185           1190           1195 gtg aag aaa gat gac atc tgg ccc tca ggg ggc caa atg act gtc aaa        3771
Val Lys Lys Asp Asp Ile Trp Pro Ser Gly Gly Gln Met Thr Val Lys
    1200           1205           1210 gat ctc aca gca aaa tac aca gaa ggt gga aat gcc ata tta gag aac        3819
Asp Leu Thr Ala Lys Tyr Thr Glu Gly Gly Asn Ala Ile Leu Glu Asn
    1215           1220           1225 att tcc ttc tca ata agt cct ggc cag agg gtg ggc ctc ttg gga aga        3867
Ile Ser Phe Ser Ile Ser Pro Gly Gln Arg Val Gly Leu Leu Gly Arg
1230           1235           1240           1245 act gga tca ggg aag agt act ttg tta tca gct ttt ttg aga cta ctg        3915
Thr Gly Ser Gly Lys Ser Thr Leu Leu Ser Ala Phe Leu Arg Leu Leu
        1250           1255           1260 aac act gaa gga gaa atc cag atc gat ggt gtg tct tgg gat tca ata        3963
Asn Thr Glu Gly Glu Ile Gln Ile Asp Gly Val Ser Trp Asp Ser Ile
    1265           1270           1275 act ttg caa cag tgg agg aaa gcc ttt gga gtg ata cca cag aaa gta        4011
Thr Leu Gln Gln Trp Arg Lys Ala Phe Gly Val Ile Pro Gln Lys Val
    1280           1285           1290 ttt att ttt tct gga aca ttt aga aaa aac ttg gat ccc tat gaa cag        4059
```

-continued

```
Phe Ile Phe Ser Gly Thr Phe Arg Lys Asn Leu Asp Pro Tyr Glu Gln
    1295                1300                1305 tgg agt gat caa gaa ata tgg aaa gtt gca gat gag gtt ggg ctc aga       4107
Trp Ser Asp Gln Glu Ile Trp Lys Val Ala Asp Glu Val Gly Leu Arg
1310                1315                1320                1325 tct gtg ata gaa cag ttt cct ggg aag ctt gac ttt gtc ctt gtg gat       4155
Ser Val Ile Glu Gln Phe Pro Gly Lys Leu Asp Phe Val Leu Val Asp
            1330                1335                1340 ggg ggc tgt gtc cta agc cat ggc cac aag cag ttg atg tgc ttg gct       4203
Gly Gly Cys Val Leu Ser His Gly His Lys Gln Leu Met Cys Leu Ala
        1345                1350                1355 aga tct gtt ctc agt aag gcg aag atc ttg ctg ctt gat gaa ccc agt       4251
Arg Ser Val Leu Ser Lys Ala Lys Ile Leu Leu Leu Asp Glu Pro Ser
    1360                1365                1370 gct cat ttg gat cca gta aca tac caa ata att aga aga act cta aaa       4299
Ala His Leu Asp Pro Val Thr Tyr Gln Ile Ile Arg Arg Thr Leu Lys
    1375                1380                1385 caa gca ttt gct gat tgc aca gta att ctc tgt gaa cac agg ata gaa       4347
Gln Ala Phe Ala Asp Cys Thr Val Ile Leu Cys Glu His Arg Ile Glu
1390                1395                1400                1405 gca atg ctg gaa tgc caa caa ttt ttg gtc ata gaa gag aac aaa gtg       4395
Ala Met Leu Glu Cys Gln Gln Phe Leu Val Ile Glu Glu Asn Lys Val
            1410                1415                1420 cgg cag tac gat tcc atc cag aaa ctg ctg aac gag agg agc ctc ttc       4443
Arg Gln Tyr Asp Ser Ile Gln Lys Leu Leu Asn Glu Arg Ser Leu Phe
        1425                1430                1435 cgg caa gcc atc agc ccc tcc gac agg gtg aag ctc ttt ccc cac cgg       4491
Arg Gln Ala Ile Ser Pro Ser Asp Arg Val Lys Leu Phe Pro His Arg
    1440                1445                1450 aac tca agc aag tgc aag tct aag ccc cag att gct gct ctg aaa gag       4539
Asn Ser Ser Lys Cys Lys Ser Lys Pro Gln Ile Ala Ala Leu Lys Glu
    1455                1460                1465 gag aca gaa gaa gag gtg caa gat aca agg ctt tag agagcagcat           4585
Glu Thr Glu Glu Glu Val Gln Asp Thr Arg Leu
1470                1475                1480 aaatgttgac atgggacatt tgctcatgga attggagctc gtgggacagt cacctcatgg     4645
aattggagct cgtggaacag ttacctctgc ctcagaaaac aaggatgaat taagttttttt   4705 tttaaaaaag aaacatttgg taaggggaat tgaggacact gatatgggtc ttgataaatg    4765
gcttcctggc aatagtcaaa ttgtgtgaaa ggtacttcaa atccttgaag atttaccact    4825
tgtgttttgc aagccagatt ttcctgaaaa cccttgccat gtgctagtaa ttggaaaggc    4885
agctctaaat gtcaatcagc ctagttgatc agcttattgt ctagtgaaac tcgttaattt    4945
gtagtgttgg agaagaactg aaatcatact tcttagggtt atgattaagt aatgataact    5005
ggaaacttca gcggtttata taagcttgta ttccttttc tctcctctcc ccatgatgtt     5065
tagaaacaca actatattgt ttgctaagca ttccaactat ctcatttcca agcaagtatt    5125
agaataccac aggaaccaca agactgcaca tcaaaatatg ccccattcaa catctagtga    5185
gcagtcagga aagagaactt ccagatcctg gaaatcaggg ttagtattgt ccaggtctac    5245
caaaaatctc aatatttcag ataatcacaa tacatcccctt acctgggaaa gggctgttat   5305
aatctttcac aggggacagg atggttccct tgatgaagaa gttgatatgc cttttcccaa    5365
ctccagaaag tgacaagctc acagaccttt gaactagagt ttagctggaa aagtatgtta    5425
gtgcaaattg tcacaggaca gcccttcttt ccacagaagc tccaggtaga gggtgtgtaa    5485
gtagataggc catgggcact gtgggtagac acacatgaag tccaagcatt tagatgtata    5545
```

-continued

```
ggttgatggt ggtatgtttt caggctagat gtatgtactt catgctgtct acactaagag    5605
agaatgagag acacactgaa gaagcaccaa tcatgaatta gttttatatg cttctgtttt    5665
ataattttgt gaagcaaaat ttttctctcta ggaaatattt attttaataa tgtttcaaac   5725
atatattaca atgctgtatt ttaaaagaat gattatgaat tacatttgta taaaataatt    5785
tttatatttg aaatattgac tttttatggc actagtattt ttatgaaata ttatgttaaa    5845
actgggacag gggagaacct agggtgatat taaccagggg ccatgaatca ccttttggtc    5905
tggagggaag ccttgggggct gatcgagttg ttgcccacag ctgtatgatt cccagccaga   5965
cacagcctct tagatgcagt tctgaagaag atggtaccac cagtctgact gtttccatca    6025
agggtacact gccttctcaa ctccaaactg actcttaaga agactgcatt atatttatta    6085
ctgtaagaaa atatcacttg tcaataaaat ccatacattt gtgt                     6129
```

<210> SEQ ID NO 2
<211> LENGTH: 1480
<212> TYPE: PRT
<213> ORGANISM: Homo Sapiens

<400> SEQUENCE: 2

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270
```

-continued

```
Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Ser Gly Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
        370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
        530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu Asn Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
```

-continued

```
            690           695           700
Ile Asn Ser Ile Arg Lys Phe Ser Ile Val Gln Lys Thr Pro Leu Gln
705                     710                     715                 720

Met Asn Gly Ile Glu Glu Asp Ser Asp Glu Pro Leu Glu Arg Arg Leu
                    725                     730                 735

Ser Leu Val Pro Asp Ser Glu Gln Gly Glu Ala Ile Leu Pro Arg Ile
                740                     745                 750

Ser Val Ile Ser Thr Gly Pro Thr Leu Gln Ala Arg Arg Gln Ser
                755                     760                 765

Val Leu Asn Leu Met Thr His Ser Val Asn Gln Gly Gln Asn Ile His
770                     775                     780

Arg Lys Thr Thr Ala Ser Thr Arg Lys Val Ser Leu Ala Pro Gln Ala
785                     790                     795                 800

Asn Leu Thr Glu Leu Asp Ile Tyr Ser Arg Arg Leu Ser Gln Glu Thr
                805                     810                 815

Gly Leu Glu Ile Ser Glu Glu Ile Asn Glu Glu Asp Leu Lys Glu Cys
                820                     825                 830

Leu Phe Asp Asp Met Glu Ser Ile Pro Ala Val Thr Thr Trp Asn Thr
835                     840                     845

Tyr Leu Arg Tyr Ile Thr Val His Lys Ser Leu Ile Phe Val Leu Ile
850                     855                     860

Trp Cys Leu Val Ile Phe Leu Ala Glu Val Ala Ala Ser Leu Val Val
865                     870                     875                 880

Leu Trp Leu Leu Gly Asn Thr Pro Leu Gln Asp Lys Gly Asn Ser Thr
                885                     890                 895

His Ser Arg Asn Asn Ser Tyr Ala Val Ile Ile Thr Ser Thr Ser Ser
                900                     905                 910

Tyr Tyr Val Phe Tyr Ile Tyr Val Gly Val Ala Asp Thr Leu Leu Ala
                915                     920                 925

Met Gly Phe Phe Arg Gly Leu Pro Leu Val His Thr Leu Ile Thr Val
                930                     935                 940

Ser Lys Ile Leu His His Lys Met Leu His Ser Val Leu Gln Ala Pro
945                     950                     955                 960

Met Ser Thr Leu Asn Thr Leu Lys Ala Gly Gly Ile Leu Asn Arg Phe
                965                     970                 975

Ser Lys Asp Ile Ala Ile Leu Asp Asp Leu Leu Pro Leu Thr Ile Phe
                980                     985                 990

Asp Phe Ile Gln Leu Leu Leu Ile Val Ile Gly Ala Ile Ala Val Val
                995                     1000                1005

Ala Val Leu Gln Pro Tyr Ile Phe Val Ala Thr Val Pro Val Ile Val
            1010                    1015                1020

Ala Phe Ile Met Leu Arg Ala Tyr Phe Leu Gln Thr Ser Gln Gln Leu
1025                    1030                    1035                1040

Lys Gln Leu Glu Ser Glu Gly Arg Ser Pro Ile Phe Thr His Leu Val
                    1045                    1050                1055

Thr Ser Leu Lys Gly Leu Trp Thr Leu Arg Ala Phe Gly Arg Gln Pro
                    1060                    1065                1070

Tyr Phe Glu Thr Leu Phe His Lys Ala Leu Asn Leu His Thr Ala Asn
                1075                    1080                1085

Trp Phe Leu Tyr Leu Ser Thr Leu Arg Trp Phe Gln Met Arg Ile Glu
                1090                    1095                1100

Met Ile Phe Val Ile Phe Phe Ile Ala Val Thr Phe Ile Ser Ile Leu
1105                    1110                    1115                1120
```

-continued

```
Thr Thr Gly Glu Gly Glu Gly Arg Val Gly Ile Ile Leu Thr Leu Ala
            1125                1130                1135
Met Asn Ile Met Ser Thr Leu Gln Trp Ala Val Asn Ser Ser Ile Asp
            1140                1145                1150
Val Asp Ser Leu Met Arg Ser Val Ser Arg Val Phe Lys Phe Ile Asp
            1155                1160                1165
Met Pro Thr Glu Gly Lys Pro Thr Lys Ser Thr Lys Pro Tyr Lys Asn
            1170                1175                1180
Gly Gln Leu Ser Lys Val Met Ile Ile Glu Asn Ser His Val Lys Lys
1185                1190                1195                1200
Asp Asp Ile Trp Pro Ser Gly Gly Gln Met Thr Val Lys Asp Leu Thr
            1205                1210                1215
Ala Lys Tyr Thr Glu Gly Gly Asn Ala Ile Leu Glu Asn Ile Ser Phe
            1220                1225                1230
Ser Ile Ser Pro Gly Gln Arg Val Gly Leu Leu Gly Arg Thr Gly Ser
            1235                1240                1245
Gly Lys Ser Thr Leu Leu Ser Ala Phe Leu Arg Leu Leu Asn Thr Glu
1250                1255                1260
Gly Glu Ile Gln Ile Asp Gly Val Ser Trp Asp Ser Ile Thr Leu Gln
1265                1270                1275                1280
Gln Trp Arg Lys Ala Phe Gly Val Ile Pro Gln Lys Val Phe Ile Phe
            1285                1290                1295
Ser Gly Thr Phe Arg Lys Asn Leu Asp Pro Tyr Glu Gln Trp Ser Asp
            1300                1305                1310
Gln Glu Ile Trp Lys Val Ala Asp Glu Val Gly Leu Arg Ser Val Ile
            1315                1320                1325
Glu Gln Phe Pro Gly Lys Leu Asp Phe Val Leu Val Asp Gly Gly Cys
            1330                1335                1340
Val Leu Ser His Gly His Lys Gln Leu Met Cys Leu Ala Arg Ser Val
1345                1350                1355                1360
Leu Ser Lys Ala Lys Ile Leu Leu Leu Asp Glu Pro Ser Ala His Leu
            1365                1370                1375
Asp Pro Val Thr Tyr Gln Ile Ile Arg Arg Thr Leu Lys Gln Ala Phe
            1380                1385                1390
Ala Asp Cys Thr Val Ile Leu Cys Glu His Arg Ile Glu Ala Met Leu
            1395                1400                1405
Glu Cys Gln Gln Phe Leu Val Ile Glu Glu Asn Lys Val Arg Gln Tyr
            1410                1415                1420
Asp Ser Ile Gln Lys Leu Leu Asn Glu Arg Ser Leu Phe Arg Gln Ala
1425                1430                1435                1440
Ile Ser Pro Ser Asp Arg Val Lys Leu Phe Pro His Arg Asn Ser Ser
            1445                1450                1455
Lys Cys Lys Ser Lys Pro Gln Ile Ala Ala Leu Lys Glu Glu Thr Glu
            1460                1465                1470
Glu Glu Val Gln Asp Thr Arg Leu
            1475                1480
```

<210> SEQ ID NO 3
<211> LENGTH: 15
<212> TYPE: PRT
<213> ORGANISM: Homo Sapiens

<400> SEQUENCE: 3

Gly Arg Ile Ile Ala Ser Tyr Asp Pro Asp Asn Lys Glu Glu Arg

```
                1               5                        10                        15

<210> SEQ ID NO 4
<211> LENGTH: 31
<212> TYPE: PRT
<213> ORGANISM: Homo Sapiens

<400> SEQUENCE: 4

Leu Trp Leu Leu Gly Asn Thr Pro Leu Gln Asp Lys Gly Asn Ser Thr
 1               5                       10                      15

His Ser Arg Asn Asn Ser Tyr Ala Val Ile Ile Thr Ser Thr Ser
             20                      25                  30
```

METHODS AND PRODUCTS FOR TREATING PSEUDOMONAS INFECTION

RELATED APPLICATION

This application is a Divisional Application of U.S. application Ser. No. 08/681,838, filed Jul. 29, 1996, now U.S. Pat. No. 6,245,735 B1, issued Jun. 12, 2001, which is incorporated by reference.

BACKGROUND OF THE INVENTION

Cystic fibrosis (CF) is a disease that arises due to mutations in the gene that codes for cystic fibrosis transmembrane conductance regulator (CFTR), which is a membrane protein involved in chloride ion secretion [1]. Although most cystic fibrosis patients develop chronic progressive disease of the respiratory system, the disease can cause damage to many other organs and tissues. For instance, pancreatic dysfunction, hepatobiliary and genitourinary diseases are all common manifestations of the cystic fibrosis disorder. The diverse array of symptoms and disorders caused by cystic fibrosis have made treatment of the disorder a difficult task. Many treatment modes have focused on improving the clinical symptoms of the particular organ affected in the patient, such as antibiotic treatments, improved nutritional care, and physiotherapy. Additionally, therapies have been developed which attempt to counteract the biochemical basis of the genetic disease, such as gene therapy with CFTR genes. None of these treatment methods, however, has been entirely successful in the treatment of cystic fibrosis.

The most serious consequence of cystic fibrosis (CF) is *Pseudomonas aeruginosa* lung infection, which by itself accounts for almost 90% of the morbidity and mortality in CF [3]. By age 12, 60–90% of CF patients are infected with *P. aeruginosa*, and most die before age 30 [3]. Pathogens such as *S. aureus* and nontypable *H. influenza* are also commonly isolated from the respiratory tract of CF patients, but only *P. aeruginosa* infection has been associated with the progressive decline in pulmonary function in these patients [4–6].

Progressive loss of pulmonary function over many years due to chronic infection with mucoid *P. aeruginosa* is the hallmark of CF, and yet the connection between lung infection and defects in chloride ion conductance have remained elusive. Smith et al. [2] recently reported defective bacterial killing by fluid obtained from airway epithelial cell cultures of CF patients. Smith et al. reported that this phenomenon was due to the inhibition of an unidentified antimicrobial factor resulting from increased levels of sodium chloride in the airway epithelial fluid.

Many of the severe cases of CF are associated with CFTR mutations leading to greatly reduced to no cell-surface expression of CFTR. The most prevalent of the CFTR mutations is the deletion of phenylalanine 508. Mutant CFTR genes having a deleted phenylalanine 508 are referred to as ΔF508. ΔF508 accounts for approximately 70% of the cystic fibrosis alleles. The ΔF508 mutation has been associated with elevated sweat chloride levels and severe physiological effects such as chronic pulmonary disease in many patients.

Pier et al. has proposed that ingestion and clearance of *P. aeruginosa* by epithelial cells could be one mechanism by which the epithelial cells protect the lungs against infection [7]. The study reported that ingestion and clearance of *P. aeruginosa* was compromised in a cell line derived from a patient with the ΔF508 CFTR mutation and was specific for *P. aeruginosa* among the respiratory pathogens evaluated [7]. Expression of wild-type CFTR by transection, or induction of membrane expression of mutant ΔF508 CFTR by growth of cells at 26° C., increased *P. aeruginosa* ingestion. Inhibition of ingestion of *P. aeruginosa* by cells in neonatal mouse lungs increased the total bacterial load in the lungs [7]. These studies showed that CFTR modulated this epithelial cell process but did not specifically indicate how CFTR was involved in the process.

SUMMARY OF THE INVENTION

The invention involves the discovery that *P. aeruginosa* binds to the cystic fibrosis transmembrane conductance regulator (CFTR) (SEQ.ID.NO.1) and, in particular, that the core portion of the lipopolysaccharide of *P. aeruginosa* binds the CFTR. The invention also involves the discovery that contacting cells expressing the CFTR with the core portion of the lipopolysaccharide of *P. aeruginosa* results in upregulation of the CFTR. Upregulation of the CFTR in epithelial mucosa further was discovered to result in better clearance of *P. aeruginosa*, and, therefore, methods for preventing, inhibiting or eradicating Pseudomal infection are provided, including subjects having cystic fibrosis. In general, these discoveries have led to methods and products using fragments of the lipopolysaccharide of *P. aeruginosa* and using fragments of the CFTR in the manufacture of pharmaceutical products, diagnostic products, research tools, and methods relating hereto.

According to one aspect of the invention, a method for upregulating CFTR expression in the tissue of a subject is provided. A CFTR expression regulator is administered to a subject in need of upregulation of CFTR expression, in an amount effective to increase CFTR expression in the tissue of the subject. The CFTR expression regulator is an isolated polysaccharide that is an LPS core moiety comprising

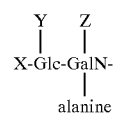

wherein X is selected from the group consisting of glucose, glucose-rhamnose and H; Y is selected from the group consisting of rhammose and H; and Z is selected from the group consisting of glucose and H;

A preferred polysaccharide is an LPS core moiety comprising

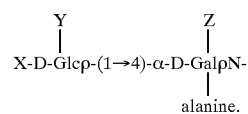

One particularly useful polysaccharide according to the invention comprises

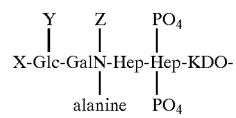

Another particularly useful polysaccharide according to the invention is:

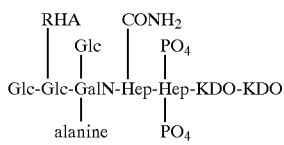

The foregoing preferred molecules can be isolated CFTR receptor-binding fragments of lipopolysaccharides of *P. aeruginosa*.

In one embodiment of the invention, the subject has a condition predisposing the subject to Pseudomal infection. In another embodiment of the invention, the subject has a Pseudomal infection. In one important embodiment of the invention, the subject has a defective cystic fibrosis transmembrane conductance regulator gene.

According to another aspect of the invention, a pharmaceutical preparation is provided. The pharmaceutical preparation is a pharmaceutically acceptable carrier and a pharmaceutically effective amount of a CFTR expression regulator. The CFTR expression regulator is as described above. The pharmaceutical preparation can be sterile and can be formulated in a unit dosage in an amount effective for treating Pseudomal infection. As used herein, "treating" means preventing the onset of, slowing the progression of, or eradicating the existence of the condition being treated, such as a Pseudomal infection. The pharmaceutical preparation can be formulated as any suitable preparation, including a preparation suitable for inhalation or a preparation suitable for injection.

According to another aspect of the invention, compositions of matter are provided. The compositions are covalent conjugates. One composition is a covalent conjugate of a lipid biocompatible with a human subject and a polysaccharide. The polysaccharide is as described above. In one embodiment, the lipid portion of the conjugate is inserted within the wall of a liposome and the polysaccharide is exposed on the surface of the liposome. The liposome contains a bioactive agent.

Another composition is a covalent conjugate of a bioactive agent and a polysaccharide. Again, the polysaccharide is as described above.

The foregoing covalent conjugates are useful in delivering bioactive agents to cells and/or tissues expressing a CFTR. Thus, methods are provided for delivering a bioactive agent to a tissue expressing a cystic fibrosis transmembrane conductance regulator to treat a condition susceptible to treatment by the bioactive agent. A bioactive agent coupled to a polysaccharide is administered to a subject in need of such treatment, in an amount effective for treating the condition. The polysaccharide is as described above. The bioactive agent can be noncovalently or covalently linked to the polysaccharide, or the bioactive agent can be contained in a liposome comprising a lipid biocompatible with a human subject, wherein the polysaccharide is covalently coupled to the lipid.

As a result of the discovery that the CFTR binds the lipopolysaccharide of *P. aeruginosa*, methods and products involving the use of CFTR fragments are provided.

According to one aspect of the invention, a composition of matter is provided. The composition is a covalent conjugate of an anti-*Pseudomonas* drug and CFTR or a lipopolysaccharide-binding fragment of a cystic fibrosis transmembrane conductance regulator. The lipopolysaccharide-binding fragment of a CFTR preferably comprises at least four consecutive amino acids of Sequence ID No. 3, and can comprise at least five, six, seven or eight consecutive amino acids of Sequence ID. No. 3.

According to another aspect of the invention, an isolated polypeptide is provided. The isolated polypeptide is a lipopolysaccharide-binding fragment of a cystic. fibrosis transmembrane conductance regulator. The fragment preferably comprises at least four consecutive amino acids of Sequence ID. No. 3, and comprise at least five, six, seven or eight consecutive amino acids of Sequence ID. No. 3. Even more preferably, the fragment is between seven and twelve amino acids in length.

According to another aspect of the invention, methods for targeting an anti-*Pseudomonas* drug to a *Pseudomonas* microorganism is provided. The method involves contacting the environment of the *Pseudomonas* with a lipopolysaccharide-binding fragment as described above coupled to an anti-*pseudomonas* drug.

According to still another aspect of the invention, isolated nucleic acids are provided. The isolated nucleic acids encode the lipopolysaccharide-binding fragments of CFTR described above.

These and other aspects of the invention are described in greater detail below. It is noted that the isolated polysaccharides of the invention, in preferred embodiments, have the more detailed structures as described below in connection with the detailed description of the invention. The se particular structures are considered important aspects of the invention.

DETAILED DESCRIPTION OF THE INVENTION

The invention involves the discovery that *P. aeruginosa* binds to CFTR and, more particularly, that the lipopolysaccharide (LPS) core of *P. aeruginosa* binds to CFTR Surprisingly, it was discovered that contacting cells expressing the CFTR with the *P. aeruginosa* LPS core resulted in upregulation of the expression of CFTR. It also was discovered, surprisingly, that such upregulation results in improved uptake of *P. aeruginosa* by such cells and improved clearance of *P. aeruginosa* by such cells, thereby providing the basis of a therapy using the core of *P. aeruginosa* LPS to inhibit, prevent or otherwise treat infection by *P. aeruginosa*. Mammals pretreated with LPS core fragments are less susceptible to infection by *P. aeruginosa*. They also recover more quickly from infection by *P. aeruginosa* than animals without such pretreatment. As a result of the foregoing discoveries, methods and products are provided that make use of CFTR binding fragments of *P. aeruginosa* LPS cores. Methods and products also are provided that make use of LPS binding-fragments of cystic fibrosis transmembrane conductance regulators. (The mRNA and amino acid sequences of CFTR are provided in SEQ.ID.NO.1 and SEQ.ID.NO.2, respectively.)

The methods and products of the invention are useful in connection with cells, microorganisms and subjects.

As used herein, a subject is a human, nonhuman primate, horse, cow, sheep, goat, dog, cat, or rodent.

As used herein in connection with polysaccharides and polypeptides, "isolated" means essentially free of other substances with which the polysaccharides or polypeptides may be found in nature or in in vivo systems to an extent practical and appropriate for their intended use. The material is sufficiently pure and sufficiently flee of other biological materials so that it may be used in, for example, a pharmaceutical preparation. The material may be isolated using conventional techniques known to those of ordinary skill in the art. The material also may be prepared by synthetic chemistry using procedures known to those of ordinary skill in the art. Because an isolated material may be admixed with a pharmaceutically acceptable carrier(s) in a pharmaceutical preparation, the material may comprise only a small percentage by weight of the preparation; it nevertheless still is isolated as is meant herein. An isolated fragment of a polypeptide or polysaccharide also is a portion of the polypeptide or polysaccharide as found in nature, isolated from the remaining portion as found in nature.

According to one aspect of the invention, a method for upregulating CFTR expression in a tissue of a subject is provided. The method involves administering to a subject in need of such upregulation a CFTR expression regulator in an amount effective to increase CFTR expression in the tissue. The CFTR expression regulator is an isolated polysaccharide that is an LPS core moiety comprising:

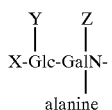

wherein X is selected from the group consisting of glucose, glucose-rhamnose and H; Y is selected from the group consisting of rhamnose and H; and Z is selected from the group consisting of glucose and H;

The entire core of the LPS of *P. aeruginosa* may be used, which consists essentially of the polysaccharide portion free of the lipid tail (which is somewhat toxic). For example, the isolated polysaccharide may be isolated from the O6 strain of *P. aeruginosa*, obtainable from the American Type Culture Collection, Rockville, Md. (ATCC) under excession no. 33354. Mutant strains of *P. aeruginosa* also are available, which strains contain the essential portions of the polysaccharide of the invention as described above, such as, for example, *Pseudomonas* strain O3, ATCC excession no. 33350.

The structure of O6 is believed to be as follows:

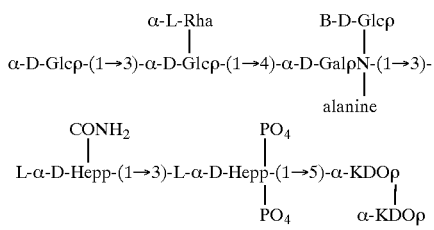

The structure of O3 is believed to be as follows:

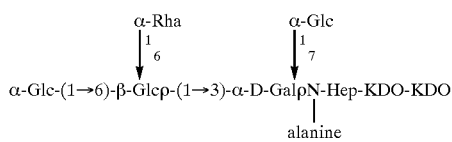

Variants derived from other mutant strains or prepared by chemical synthesis are useful according to the invention. The following variants are specific examples:

Variant I:

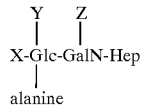

Variant II:

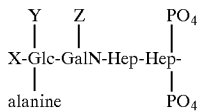

Variant III:

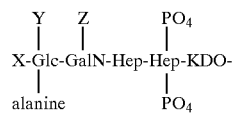

It is believed that the most preferable bonding configuration is

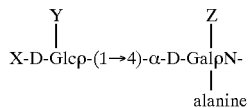

Those of ordinary skill in the art will be able to identify other variants and modifications useful according to the invention Synthetic chemistry for constructing small polysaccharides is available. In addition, core polysaccharides can be derived from the many and various mutant strains of *P. aeruginosa*. These materials then may be simply tested for binding to the CFTR, the sequence of which is provided herein as Sequence ID. No. 1. The CFTR gene is the subject of gene therapy clinical protocols and has been studied extensively in various expression systems, many of which would be suitable for screening LPS core variant binding. The CFTR or the polysaccharide also could be bound to a substrate, such as a polystyrene plate. Screening experiments could involve direct measurement of the binding of the variant to CFTR if the variant were labeled, such as with a radioactive label or a florescent label. Likewise, the CFTR could be labeled in direct binding studies. Screening also can be carried out by measuring indirect binding such as in a competitive binding assay. Such assays could involve competition with *P. aeruginosa* binding to CFTR or with isolated core LPS of *P. aeruginosa* binding to CFTR. Those of ordinary skill in the art will readily know the details of such screening assays.

As mentioned above, the invention involves the surprising discovery that the polysaccharides of the invention upregulate CFTR expression and can result in increased uptake of *P. aeruginosa* and clearance of *P. aeruginosa*. Increased CFTR expression can be evaluated, for example, by measuring CFTR mRNA, by using antibodies against the CFTR, or by measuring LPS core binding to the CFTR Such measurements are well within the ability of those of ordinary skill in the art.

The invention is useful in treating a variety of conditions involving the CFTR. Most notably, the invention is useful whenever it is desirable to prevent, inhibit or halt infection by *P. aeruginosa*. This includes treating subjects having conditions that predispose the subjects to infection by *P. aeruginosa*, such as patients requiring medical intensive care (including surgical intensive care), patients with a basic compromise to the respiratory tract (such as by intubation), patients are immuno-compromised such as by anticancer chemotherapy treatment and patients with chronic obstructive pulmonary disease. Treatment can be prophylactic or can be concurrent with active infection. It is believed that frequent (daily) treatment will be most successful.

In the foregoing instances, the patients can have normal CFTRs. The invention is also useful when the patient's CFTRs are not normal, such as with cystic fibrosis patients who have a defective CFTR gene. In some instances, it is believed that a defective CFTR still will bind *P. aeruginosa*, although weakly and inadequately. Thus, upregulation of a defective CFTR also will enhance clearance of *P. aeruginosa*, and, therefore, the polysaccharides of the invention are useful in treating subjects with defective CFTR genes.

It is noted that CFTR is expressed in a variety of tissues and is believed to have functions in addition to simply binding and clearing *P. aeruginosa*. The receptor is expressed in the gastrointestinal tract (intestinal epithelial cells), in the goblets within the respiratory tract, in genital tissue, in kidney tissue, in pancreas tissue, in liver tissue, and in corneal epithelial cells. Some of the negative effects of a defective CFTR gene are managed by diet, and it is believed that upregulation of the defective receptor would be of benefit in these situations. Negative effects of a defective CFTR include malabsorption in the gastrointestinal tract (managed by diet and by patients taking pancreatic supplements, but patients are still usually in the lower 5th percentile for weight and height); sterility in males (genitouriny tract); on occasion, diabetes (pancreas) and arthritis. The polysaccharides of the invention, therefore, are useful whenever it is desirable to upregulate CFTR expression, whether the CFTR gene is normal or defective.

The presence of the CFTR in a variety of tissues also has led to another aspect of the invention, that is the use of the isolated polysaccharides of the invention to target a bioactive molecule to a tissue expressing a CFTR. The CFTR binding fragment of a LPS of *P. aeruginosa* is used as a targeting moiety in an otherwise conventional manner, to target bioactive agents to tissues expressing the CFTR. In general the targeting moiety is coupled to the bioactive agent. The molecules may be directly coupled to one another, such as by conjugation or may be indirectly coupled to one another where, for example, the targeting moiety is on the surface of the liposome and the bioactive agent is contained within the liposome. Thus, the invention contemplates conjugates of the isolated polysaccharides of the invention with bioactive agents. If the molecules are linked to one another, then the targeting moiety is covalently or noncovalently bound to the bioactive agent in a manner that preserves the targeting specificity of the targeting moiety. As used herein, "linked" or "linkage" means two entities are bound to one another by any physiochemical means. It is important that the linkage be of such a nature that it does not impair substantially the effectiveness of the bioactive molecule or the binding specificity of the targeting moiety. Keeping these parameters in mind, any linkage known to those of ordinary skill in the art may be employed, covalent or noncovalent. Such means and methods of linkage are well known to those of ordinary skill in the art.

Linkage according to the invention need not be direct linkage. The components of the compositions of the invention may be provided with functionalized groups to facilitate their linkage and/or linker groups may be interposed between the components of these compositions to facilitate their linkage. In addition, the components of the present invention may be synthesized in a single process, whereby the components could be regarded as one in the same entity. For example, a targeting moiety specific for a CFTR receptor could be synthesized together with the bioactive agent. These and other modifications are intended to be embraced by the present invention.

Specific examples of covalent bonds include those wherein bifunctional cross-linker molecules are used. The cross-inker molecules may be homobifunctional or heterobifunctional, depending upon the nature of the molecules to be conjugated. Homobifunctional cross-linkers have two identical reactive groups. Heterobifunctional cross-linkers have two different reactive groups that allow sequential conjugation reaction. Various types of commercially available cross-linkers are reactive with one or more of the following groups: primary amines, secondary amines, sulfhydriles, carboxyls, carbonyls and carbohydrates.

Non-covalent methods of conjugation also may be used to join the targeting moiety and the bioactive agent. Non-covalent conjugation may be accomplished by direct or indirect means including hydrophobic interaction, ionic interaction, intercalation, binding to major or minor grooves of a nucleic acid and other affinity interactions.

Covalent linkages may be noncleavable in physiological environments or cleavable in physiological environments, such as linkers containing disulfide bonds. Such molecules may resist degradation and/or may be subject to different intracellular transport mechanisms. One of ordinary skill in the art will be able to ascertain without undue experimentation the preferred bond for linking the targeting moiety and the bioactive agent, based on the chemical properties of the molecules being linked and the preferred characteristics of the bond.

For indirect linkage, the targeting moiety may be part of a particle, such as a liposome, which targets the liposome to tissues expressing the CFTR. The liposome, in turn, may contain the bioactive agent. The manufacture of liposomes containing bioactive agents is fully described in the literature. Many are based upon cholesteric molecules as starting ingredients and/or it phospholipids. They may be synthetically derived or isolated from natural membrane components. According to an embodiment of the invention, the polysaccharide which is the All targeting moiety is attached to a non-toxic, lipophilic anchor that is biocompatible with a human subject. Virtually any hydrophobic substance can be used, including cholesteric molecules, phospholipids and fatty acids preferably of medium chain length (12C–20C). Preferred are naturally occurring fatty acids of between 14 and 18 carbons in length. These molecules can be attached to the polysaccharides of the invention, with the lipophilic anchor inserting into the membrane of a liposome and the polysaccharide tethered on the surface of the liposome for targeting the liposome to the cell expressing the CFTR.

It is noted that lipid A normally is attached to native lipopolysaccharide of *P. aeruginosa*. Lipid A, however, is somewhat toxic, and it is preferred that the polysaccharides of the invention, if attached to lipophilic molecules, be attached to molecules which have a better toxicity profile than Lipid A. Useful lipophilic moieties may include any short to medium-chain length saturated fatty acid of the general composition $CH_3(CH_2)_nCOOH$ where n can range from 0–50. Preferably n will range from 1–20. In addition, the $CH_2$ groups may be modified to be linked to each other through double-carbon bonds, making the fatty acid of the unsaturated category. Further modifications could include additional substituents such as hydroxyl (OH) groups added on to the fatty acid chain backbone to produce hydroxylated fatty acids. The substituents may be added to either the same side of the fatty acid chain (the trans-configuration) or to opposite sides of the fatty acid chain (the cis configuration). The lipophilic moieties may be attached to the targeting moieties as described above.

The bioactive agent may be virtually any bioactive agent useful in a cell expressing a CFTR Bioactive agents, as used herein, include diagnostic agents such as radioactive labels and fluorescent labels. Bioactive agents also include molecules affecting the metabolism of a cell expressing a CFTR, including peptides, nucleic acids, and other natural and synthetic drug molecules. Included are: adrenergic agent; adrenocortical steroid; adrenocortical suppressant; alcohol deterrent; aldosterone antagonist; amino acid; ammonia detoxicant; anabolic; analeptic; analgesic; androgen; anesthesia, adjunct to; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; anti-emetic; anti-epileptic; antiestrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; blood glucose regulator, bone resorption inhibitor; bronchodilator, carbonic anhydrase inhibitor; cardiac depressant; cardioprotectant; cardiotonic; cardiovascular agent; choleretic; cholinergic; cholinergic agonist; cholinesterase deactivator, coccidiostat; cognition adjuvant; cognition enhancer, depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; inmmunoregulator, immunostimulant; immunosuppressant; impotence therapy adjuvant; inhibitor; keratolytic; LHRH agonist; liver disorder treatment; luteolysin; memory adjuvant; mental performance enhancer; mood regulator, mucolytic; mucosal protective agent; mydriatic; nasal decongestant; neuromuscular blocking agent; neuroprotective; NMDA, antagonist; non-hormonal sterol derivative; oxytocic; plasminogen activator, platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine A1 antagonist; serotonin antagonist; serotonin inhibitor, serotonin receptor antagonist; steroid; stimulant; suppressant; symptomatic multiple sclerosis; synergist; thyroid hormone; thyroid inhibitor; thyromimetic; tranquilizer; amyotrophic lateral sclerosis agent; cerebral ischemia agent; Paget's disease agent; unstable angina agent; uricosuric; vasoconstrictor, vasodilator, vulnerary; wound healing agent; xanthine oxidase inhibitor.

In one preferred embodiment, a gene under the control of a promoter, preferably in a plasmid, is coupled to the targeting moiety for delivering the gene to the cell expressing the CFTR. In one particularly important embodiment, the gene is a normal CFTR gene and the methods and products of the invention are used to treat subjects with defective CFTR genes by gene therapy. A gene therapy contruct for CF, for example, may include either the cDNA sequence of CFTR incorporated into an appropriate expression system, or the genomic DNA sequence of CFTR including the coding exons and noncoding introns incorporated into an appropriate expression vector. It could also be a contruct containing only a portion of the CFTR that is needed to restore normal cellular function. For example, the first 150 amino acids are not needed for chloride ion conductance of the cell and this portion of CFTR could be produced from an appropriate cDNA or genomic DNA. Alternately, the portion of CFTR encoding the *P. aeruginosa* binding site (amino acids 103–118) could be expressed only in lung cells to promote resistance to infection since the rest of the molecule, which has ion-secretion properties, is not needed for resistance to infection. Antisense molecules can be delivered according to the methods of the invention as well. Thus, an important aspect of the invention is the targeting and delivery of oligonucleotides to cells expressing the CFTR.

Because of the discovery that CFTR binds *P. aeruginosa* LPS core, this has led to the further aspects of the invention related to the use of CFTR or CFTR fragments for therapeutic, diagnostic and research purposes as well as in vivo and in vitro methods relating thereto. Thus, according to another aspect of the invention, compositions of matters are provided that involve CFTR and fragments of the CFTR. In one aspect of the invention, a covalent conjugate of an anti-*Pseudomonas* drug and CFTR or a *Pseudomonas* lipopolysaccharide-binding fragment of CFTR is provided. The lipopolysaccharide-binding fragment comprises at least four consecutive amino acids of SEQ ID NO. 3. The fragment can comprise at least five consecutive amino acids, at least six consecutive amino acids, at least seven consecutive amino acids, or at least eight consecutive amino acids of SEQ ID NO. 3. SEQ ID NO. 3 consists of amino acids numbered 103–117 of the coding region of the CFTR. Thus, where at least four consecutive amino acids from SEQ ID NO. 3 are involved, there are twelve possibilities as follows: amino acids numbered 103–106, 104–107, 105–108, 106–109, 107–110, 108–111, 109–112, 110–113, 111–114, 112–115, 113–116 and 114–117. Where at least five consecutive amino acids are involved, there are eleven possibilities as follows: amino acids numbered 103–107, 104–108, 105–109, 106–110, 107–111, 108–112, 109–113, 110–114, 111–115, 112–116 and 113–117. Where there are at least six consecutive amino acids involved, there are ten possibilities as follows: amino acids numbered 103–108, 104–109, 105–110, 106–111, 107–112, 108–113, 109–114, 110–115, 111–116 and 112–117. Where there are at least seven consecutive amino acids involved, there are nine possibilities as follows: amino acids numbered 103–109, 104–110, 105–111, 106–112, 107–113, 108–114, 109–115, 110–116 and 111–117. Where there are eight consecutive amino acids involved, there are eight possibilities as follows: amino acids numbered 103–110, 104–111, 105–112, 106–113, 107–114, 108–115, 109–116 and 110–117.

It is believed that the optimal fragments will be between six and twelve amino acids in length, preferably between six and eight amino acids in length.

Determining the optimum sequence and number of amino acids for optimum binding to LPS can be determined with no more than routine experimentation. Segments of SEQ ID NO. 3 can be readily synthesized and binding experiments with, for example, immobilized *P. aeruginosa* lipopolysaccharide core can be carried out. The assay can be direct, as with radioactive labeled fragments of SEQ ID NO. 3 or can be indirect such as using competitive binding assays between SEQ ID NO. 3 and fragments of SEQ ID NO. 3. The invention thus contemplates the essential and optimal binding fragment of SEQ ID NO. 3.

The isolated lipopolysaccharide-binding fragments of a cystic fibrosis transmembrane conductance regulator can be labeled or coupled to a drug for targeting *P. aeruginosa* in vitro or in vivo. The anti-*Pseudomonas* drug can be any drug effective in either diagnosing a Pseudomal infection or in treating a Pseudomal infection. Such drugs include antimicrobials, antimicrobial potentiating agents, immune system recognition enhancers, diagnostic molecules and the like.

Molecules useful as antimicrobials can be delivered by the methods and compositions of the invention, such that the pathogenic infection is reduced or eliminated. Anti-Pseudomal agent drugs can be bactericidal or bacteriostatic by inhibiting replication of bacteria or inhibiting synthesis of bacterial components required for survival of the infecting organism. Anti-*Pseudomonas* antibiotic include the following: Amifloxacin; Amifloxacin Mesylate; Amikacin; Amikacin Sulfate; Aminosalicylic acid; Aminosalicylate sodium; Azlocillin; Azlocillin Sodium; Bacampicillin Hydrochloride; Carbenicillin Disodium; Carbenicillin Indanyl Sodium; Carbenicillin Phenyl Sodium; Carbenicillin Potassium; Carumonam Sodium; Cefactor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuoroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chlortetracycline Bisulfate; Chlortetracycline Hydrochloride; Ciprofloxacin; Ciprofloxacin Hydrochloride; Colistin Sulfate; Coumermycin; Coumermycin Sodium; Doxycycline; Doxycycline Calcium; Doxycycline Fosfatex; Doxycycline Hyclate; Droxacin Sodium; Enoxacin; Epicillin; Epitetracycline Hydrochloride; Imipenem; Kanamycin Sulfite; Meclocycline; Minocycline; Minocycline Hydrochloride; Nafcillin Sodium; Norfloxacin; Ofloxacin;Oxytetracycline; Oxytetracycline Calcium; Piperacillin Sodium; Pirbenicillin Sodium; Tetracycline; Tetracycline Hydrochloride; Tetracycline Phosphate Complex; Ticarcillin Cresyl Sodium; Ticarcillin Disodium; Ticarcillin Monosodium; Tobramycin; and Tobramycin Sulfate.

The foregoing molecules may be coupled to CFTR or the fragment of CFTR that acts as the targeting moiety by the methods as described above in connection with the LPS-core targeting moiety.

The invention also involves isolated nucleic acids that encode the fragments of CFTR described above. Such nucleic acids are useful in producing the fragments described above. The nucleic acids can be part of an expression vector and can be included within a host cell. Virtually any cells, prokaryotic or eukaryotic, which can be transformed with CFTR DNA or RNA and which can be grown or maintained in culture may be used in the practice of the invention. Examples include bacterial cells such as *E. coli* and mammalian cells such as mouse, hamster, pig, goat, primate, etc. Specific examples include CHO cells and COS cells. Cell-free transcription systems also may be used in lieu of cells.

When used therapeutically, the compounds of the invention are administered in therapeutically effective amounts. In general, a therapeutically effective amount means that amount necessary to delay the onset of, inhibit the progression of, ameliorate the symptoms of or halt altogether the particular condition being treated. It is less than that amount that produces medically unacceptable side-effects. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg and most preferably from about 0.2 mg/kg to about 20 mg/kg, in one or more dose administrations daily, for one or more days.

The therapeutics of the invention can be administered by any conventional route, including injection or by inhalation. The administrations may, for example, be oral, intravenous, intraperitoneal, intramuscular, intracavity, subcutaneous, or transdermal. When the subject has cystic fibrosis, a preferred route of administration is by pulmonary aerosol. Techniques for preparing aerosol delivery systems are well known to those of skill in the art. Generally, such systems should utilize components which will not significantly impair the biological properties of the therapeutic, such as the binding capacity of the polysaccharide (see, for example, Sciarra and Cutie, "Aerosols," in *Remington's Pharmaceutical Sciences*, 18th edition, 1990, pp 1694–1712; incorporated by reference). Those skill in the art can readily determine the various parameters and conditions for producing aerosols without resort to undue experimentation.

Preparations for parenteral administration include sterile aqueous or non-aqueous solutions suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy also is contemplated according to the invention. Gene therapy for cystic fibrosis is underway in clinical trials, and various vectors for expressing CFTR are known to those skilled in the art.

Certain of the various objects and advantages of the invention are illustrated in the following examples. Numerous equivalents and embodiments will be apparent to those of ordinary skill in the art and are intended to be embraced by the appended claims.

EXAMPLE 1

CFTR is the Cellular Receptor for *P. aeruginosa* Internalization

Materials and Methods:

Cell lines. CFT1-LCFSN cells, carrying a retrovirally introduced chromosomal copy of the wild-type human CFTR gene were kindly provided by J. Olsen, J. Yankaskis and L. Johnson from The University of North Carolina, Chapel Hill, N.C. [8,9]. The cell line parental to CFT1-LCFSN is designated CFT1; it is a line of human papilloma virus 18 E6/E7 transformed bronchial epithelial cells derived from a CF patient homozygous for ΔF508 CFTR. The CFT1-LCFSN cells have normal chloride ion conductance [8,9]. CFT1-ΔF508 cells are derived from CFT1 cells and carry a cDNA introduced by a retrovirus vector that encodes the ΔF508 mutant form of CFTR. Cells were grown in supplemented F-12 medium as described [8] in 5% $CO_2$ at 37° C.

C127 cells expressing wild-type or ΔF508 CFTR were obtained from Genzyme Corp., Framingham, Mass. [10] C127 cells were grown in RPMI medium with 2.5 grams dextrose/liter, supplemented with glutamine, non-essential amino acids, sodium pyruvate, 2-mercaptoethanol, 10% fetal bovine serum and 400 $\mu$g G418/ml. Parental cells were grown without the G418. Cells were released from monolayers in tissue culture flasks by 5 min. of incubation with trypsin-versene mixture (BioWhitaker, Walkersville, Md.), washed, counted and seeded into 96-well tissue culture plates at $10^5$ cells/well in supplemented F-12 medium and incubated at 37° C. in 5% $CO_2$.

WI-38 (human diploid lung cell line, ATCC. no. CCL-75) and A549 cells (human lung carcinoma cells, ATCC no. CCL-185) were obtained from the ATCC and grown according to their instructions.

Bacterial strains. *P. aeruginosa* strains used include PAO1, a well-characterized laboratory strain, and strains 149 and 324, non-mucoid, LPS-smooth clinical isolates of *P. aeruginosa* from CF patients early in the course of infection. Fresh cultures of *P. aeruginosa* grown overnight at 37° C. on a tryptic soy agar plate were suspended in supplemented medium to prepare the bacterial inoculum. Approximately $10^6$ cfu of the bacterial inoculum were added per well of $10^5$, epithelial cells.

Reagents for inhibition of ingestion assays. Membranes were prepared from C127 cells as described by O'Riordan et al. [11]. Membranes were suspended in 150 mM NaCl, 50 mM Tris, pH 7.5 and 1 mM EDTA and added at the indicated concentration to suspensions of *P. aeruginosa* strains prior to adding this mixture to CFT1-LCFSN cells to measure bacterial uptake. Membranes from CEM/VbI cells expressing P-glycoprotein and membranes from control CEM cells lacking P-glycoprotein were obtained from James Croop of Harvard Medical School. Purified (~85%) recombinant CFTR was obtained from Genzyme Corp., and prepared as described [11]. The protein was solubilized in 100 mM NaCl, 10 mM Tris, pH 8.0, 2 mM di-thio-threitol and 0.1% sodium dodecyl sulfate. Monoclonal antibodies raised to synthetic peptides corresponding to the first (MAb CF3) and fourth (MAb CF4) predicted extracellular domains of CFTR, as well as a MAb specific to a peptide representing the carboxy-terminal 14 amino acids of mature CFTR (MAb CF2) were provided by Dr. George Banting, University of Bristol, Bristol, UK [12]. Synthetic peptides were obtained from Chiron Mimetopes, San Diego, Calif. Peptide GRIASYDPDNKEER (15 amino acids) (SEQ.ID.NO. 3) represents amino acids 103–117 of mature CFTR, peptide LWLLGNTPLQDKGNSTHSRNNSYAVIITSTS (31 amino acids) (SEQ.ID.NO. 4) represents amino acids 881–911 of mature CFTR. Peptides were made up as a stock solution in F-12 medium containing 1 $\mu$M/$\mu$l based on the purity reported by the manufacturer. Peptides were diluted in F-12 tissue culture medium prior to use in assays.

Bacterial ingestion assay. Cells were released from monolayers in tissue culture flasks by 5 min. of incubation with trypsin-versene mixture (BioWhitaker, Walkersville, Md.), washed, counted and seeded into 96-well tissue culture plates at $10^5$ cells/well in supplemented F-12 medium [8] and incubated at 37° C. in 5% $CO_2$. Fresh cultures of *P. aeruginosa* grown overnight at 37° C. on a tryptic soy agar plate were suspended in supplemented F-12 medium to prepare the bacterial inoculum. Then $10^6$ colony forming units (cfu) of the bacterial inoculum were added per well of $10^5$ epithelial cells. Bacteria were allowed to invade the epithelial cells for 3 to 4 hours at 37° C., after which nonadherent bacteria were removed by washing. The remaining steps of the assay and the steps involved in the controls have previously been described [13]. Three to 9 replicates were obtained per point, and analyzed using analysis of variance (ANOVA) and the Fisher PLSD statistic to determine pairwise differences [14].

Inhibition of ingestion in the presence of membranes isolated from C127 cells, monoclonal antibodies to extracellular domains of CFTR, or synthetic peptides corresponding to the first or fourth extracellular domains of CFTR was evaluated by adding these materials to the bacteria prior to adding them directly into wells for evaluation of bacterial uptake.

Augmentation of ingestion was tested by incubating cultures of $10^5$ cells in 96-well plates with complete or incomplete lipopolysaccharide (LPS) core oligosaccharide isolated from *P. aeruginosa* strains PAC557 or PAC1R(algC::tet), [15] respectively, as described [7]. The oligosaccharides were added at various concentrations for 24 hours then cells washed extensively with tissue-culture medium prior to adding bacteria for internalization assays.

Neonatal mouse model of infection. Seven-day old neonatal Balb/c mice were infected with ~$10^8$ cfu of stain PAO1 delivered intranasally as described [16], with the addition of 10 nM of a synthetic peptide corresponding to either the first or fourth extracellular domains of CFTR to the bacterial inoculum. Twenty-four hours later 7 animals were killed, right and left lungs removed, weighed and dispersed into single cell suspensions by grinding through a fine-mesh wire screen. An aliquot was removed, Triton X-100 added to a final concentration of 0.5% to release intracellular bacteria and the total cfu of bacteria present in each lung determined. The remaining portion of the lung cell suspension was treated with 300 $\mu$g gentamicin/ml for 60 minutes to kill extracellular *P. aeruginosa*. The cells were then pelleted in a centrifuge (400×g, 10 minutes), washed twice in RPMI medium, and resuspended in 200 µl of 0.5% Triton X-100 to release intracellular bacteria that survived the gentamicin treatment. These suspensions were diluted and plated for bacterial enumeration. The cfu per milligram lung weight was calculated and differences among groups analyzed by nonparametric statistics (Mann-Whitney U test) due to outliers in some groups [14].

Results:

To determine if CFTR is a receptor for *P. aeruginosa* internalization, bacterial uptake assays using transformed murine epithelial C127 cells stably transfected with cDNA encoding either wild-type or ΔF508-mutant CFTR were carried out. Cells were prepared and treated as described above under the heading Bacterial Ingestion Assay and the amount of bacteria ingested by the cells was measured as mean colony forming units (CFU). In comparison to the parental C127 line (C127 parent), and the line transfected with mutant ΔF508 CFTR (C127-ΔF508), cells expressing wild-type human CFTR (C127-WT) had significantly enhanced uptake of three isolates of *P. aeruginosa* (Table 1). The data of Table 1 indicates that the WT CFTR is involved in the ingestion of *P. aeruginosa* because the cells transfected with the WT CFTR are capable of ingesting more *P. aeruginosa* than cells transfected with the mutant CFTR.

TABLE 1

Ingestion of various strains of Pseudomonas aeruginosa
(Mean colony forming units (standard deviation) of *P. aeruginosa*
strain ingested by the C127 cells)

| P. aeruginosa | C127 parent | C127-ΔF508 | C127-WT |
|---|---|---|---|
| 149 | $6.6 \times 10^3$ | $8.583 \times 10^3$ | $7.2183 \times 10^4$ |
|  | $(1.1355 \times 10^3)$ | $(2.938 \times 10^3)$ | $(7.605 \times 10^3)$ |
| 324 | $7.517 \times 10^3$ | $1.8767 \times 10^4$ | $5.5717 \times 10^4$ |
|  | $(3.339 \times 10^3)$ | $(2.655 \times 10^3)$ | $(1.4534 \times 10^4)$ |
| PAO1 | $1.9 \times 10^4$ | $4.6 \times 10^4$ | $1 \times 10^5$ |
|  | $(1.192 \times 10^4)$ | $(1.59 \times 10^4)$ | $(5.59 \times 10^3)$ |

Based on the above experiment, it was hypothesized that WT CFTR expressed on the cell surface might be interacting with the LPS. If this were correct, then exogenously added CFTR should be able to inhibit the interaction between *P. aeruginosa* and cells expressing the WT CFTR. To test this hypothesis membranes isolated from the tree C127 cell lines were added to cultures of *P. aeruginosa* and then the mixture was added to the transformed human airway epithelial cell line CFT1-LCFSN (originally derived from a CF patient homozygous for the ΔF508 mutation and subsequently transfected with wild-type CFTR DNA) (Table 2). While incubating the *P. aeruginosa* with the membranes derived from C127 cells expressing wild-type CFTR inhibited epithelial cell uptake of *P. aeruginosa*, neither the C127 parent cells not the C127-ΔF508 cells inhibited uptake. This suggests that the CFTR on the surface of airway epithelial cells is specifically interacting with the LPS and mediating its uptake.

TABLE 2

Inhibition of internalization of *P. aeruginosa* strain PAO1 into transformed human airway epithelial cells (CFT1-LCFSN line).
[Mean cfu *P. aeruginosa* internalized (standard deviation)

| Amount Inhibitor | Parental cells (no CFTR) | ΔF508 CFTR | Wild-type CFTR |
|---|---|---|---|
| 250 µg | $7.49 \times 10^4$ | $9.3383 \times 10^4$ | $1.0383 \times 10^4$ |
|  | $(1.2878 \times 10^4)$ | $(2.0009 \times 10^4)$ | $(1.986 \times 10^3)$[a] |

TABLE 2-continued

Inhibition of internalization of *P. aeruginosa* strain PAO1 into transformed human airway epithelial cells (CFT1-LCFSN line).
[Mean cfu *P. aeruginosa* internalized (standard deviation)

| 100 µg | $8.0117 \times 10^4$ | $6.7533 \times 10^4$ | $4.6683 \times 10^4$ |
|---|---|---|---|
|  | $(1.3263 \times 10^4)$ | $(6.426 \times 10^3)$ | $(6.53 \times 10^3)$[a] |
| 25 µg | $8.375 \times 10^4$ | $8.1133 \times 10^4$ | $5.6983 \times 10^4$ |
|  | $(3.5746 \times 10^4)$ | $(2.2992 \times 10^4)$ | $(2.409 \times 10^3)$[a] |
| 10 µg | $6.535 \times 10^4$ | $6.39 \times 10^4$ | $6.595 \times 10^4$ |
|  | $(3.481 \times 10^3)$ | $(5.92 \times 10^3)$ | $(5.914 \times 10^3)$ |

| Controls | | | |
|---|---|---|---|
| No inhibitor | | | $9.858 \times 10^4$ $(2.228 \times 10^4)$ |
| P glycoprotein[b] | | | $9.2567 \times 10^4$ $(3.5815 \times 10^4)$ |
| Control membranes[c] | | | $9.3217 \times 10^4$ $(1.9863 \times 10^4)$ |

[a]Significantly less cfu of *P. aeruginosa* internalized compared to inhibition with membranes from parental C127 cells or membranes from C127 cells expressing the ΔF508 mutant of CFTR at P <.01, ANOVA
[b]P glycoprotein in 50 µg of membranes from CEM/Vbl cells
[c]control membranes from CEM cells lacking P-glycoprotein Furthermore, when highly purified (~85%) recombinant CFTR was added to a culture of *P. aeruginosa* prior to addition to tissue culture wells containing CFT1-LCFSN cells, significant inhibition of bacterial ingestion was obtained with nanogram quantities of CFTR (Table 3). These results strongly implicate CFTR as the epithelial-cell ligand for internalization of *P. aeruginosa*.

TABLE 3

Inhibition of internalization of *P. aeruginosa* strain PAO1 into transformed human airway epithelial cells (CFT1-LCFSN line) by highly purified recombinant CFTR mean cfu *P. aeruginosa* internalized (standard deviation)

| CONCENTRATION OF PROTEIN/ml | BSA | CFTR |
|---|---|---|
| 5000 µg protein | $9.2 \times 10^4$ $(3.9 \times 10^4)$ | $1.65 \times 10^4$ $(1.05 \times 10^4)$[a] |
| 625 µg protein | $8.3 \times 10^4$ $(1.65 \times 10^4)$ | $4.9 \times 10^4$ $(1.25 \times 10^4)$[a] |
| 78 µg protein | $9.55 \times 10^4$ $(2.55 \times 10^4)$ | $8.55 \times 10^4$ $(1.15 \times 10^4)$ |
| 9.7 µg protein | $8.55 \times 10^4$ $(2.8 \times 10^4)$ | $1.05 \times 10^5$ $(2.5 \times 10^4)$ |
| (control) 0.0 (Tissue culture media only) | $1.58 \times 10^5$ $(3.6 \times 10^4)$ | |
| 0.0 (Media + protein solubilization buffer)[b] | $1.475 \times 10^5$ $(1.4 \times 10^4)$ | |

[a]Significantly different from inhibition with BSA, P <.01, unpaired t-test.
[b]Tissue culture media plus 0.1% Tris-SDS buffer used to solubilize CFTR

EXAMPLE 2

Identification of the Domain of CFTR that Interacts with *P. aeruginosa*

Results:

To identify the extacellular domain of CFTR that interacts with *P. aeruginosa*, monoclonal antibodies (Mab) were raised to synthetic peptides corresponding to the first (MAb CF3) and fourth (MAb CF4) predicted extracellular domains of CFTR, as well as a MAb specific to a peptide representing the carboxy-terminal 14 amino acids of mature CFTR (MAb CF2) [12]. Addition of these MAbs in various concentrations to cultures of three *P. aeruginosa* strains prior to their addition to the CFT1-LCFSN cells resulted in a concentration-dependent inhibition of internalization of *P. aeruginosa* by MAb CF3. This inhibitory effect was not observed with the other MAbs (Tables 4A, 4B and 4C).

TABLE 4A

Inhibition of internalization of *P. aeruginosa* strain PAO1 into transformed human airway epithelial cells (CFT1-LCFSN line) by monoclonal antibodies (MAbs) specific to extracellular domains of CFTR

[mean cfu of *P. aeruginosa* internalized (standard deviation)]

| MAb dilution | C-terminus (Mab CF2) | 4th Outer Domain (Mab CF4) | First Outer Domain (Mab CF3) |
|---|---|---|---|
| 2   | $4.51 \times 10^4$ $(8.061 \times 10^3)$ | $4.75 \times 10^4$ $(5.491 \times 10^3)$ | $4.45 \times 10^3$ $(1.307 \times 10^3)^a$ |
| 10  | $4.4517 \times 10^4$ $(5.283 \times 10^3)$ | $5.085 \times 10^4$ $(3.369 \times 10^3)$ | $1.4667 \times 10^4$ $(4.556 \times 10^3)^a$ |
| 25  | $5.0733 \times 10^4$ $(3.721 \times 10^3)$ | $5.145 \times 10^4$ $(4.06 \times 10^3)$ | $4.285 \times 10^4$ $(3.635 \times 10^3)^a$ |
| 100 | $4.6067 \times 10^4$ $(6.397 \times 10^3)$ | $4.7583 \times 10^4$ $(6.651 \times 10^3)$ | $4.908 \times 10^4$ $(3.832 \times 10^3)$ |
| 0   | $5.6933 \times 10^4$ $(4.505 \times 10^3)$ | $5.6933 \times 10^4$ $(4.505 \times 10^3)$ | $5.6933 \times 10^4$ $(4.505 \times 10^3)$ |

[a]Significantly fewer internalized *P. aeruginosa* bacteria in the presence of MAbs specific to the other domains of CFTR, or no MAb at $P < .001$, ANOVA

TABLE 4B

Inhibition of internalization of *P. aeruginosa* strain 149 into transformed human airway epithelial cells (CFT1-LCFSN line) by monoclonal antibodies (MAbs) specific to extracellular domains of CFTR

[mean cfu of *P. aeruginosa* internalized (standard deviation)]

| MAb dilution | C-terminus (Mab CF2) | 4th Outer Domain (Mab CF4) | First Outer Domain (Mab CF3) |
|---|---|---|---|
| 2   | $1.1067 \times 10^4$ $(1.61 \times 10^3)$ | $1.8033 \times 10^4$ $(1.041 \times 10^3)$ | $6.7 \times 10^1$ $(1.21 \times 10^2)^a$ |
| 10  | $1.6117 \times 10^4$ $(2.568 \times 10^3)$ | $1.6517 \times 10^4$ $(2.372 \times 10^3)$ | $3.33 \times 10^2$ $(3.78 \times 10^2)^a$ |
| 25  | $1.375 \times 10^4$ $(1.78 \times 10^3)$ | $1.4586 \times 10^4$ $(5.989 \times 10^3)$ | $6.067 \times 10^3$ $(5.85 \times 10^2)^a$ |
| 100 | $1.57 \times 10^4$ $(2.338 \times 10^3)$ | $1.675 \times 10^4$ $(1.924 \times 10^3)$ | $1.6233 \times 10^4$ $(1.532 \times 10^3)$ |
| 0   | $1.685 \times 10^4$ $(2.512 \times 10^3)$ | $1.685 \times 10^4$ $(2.512 \times 10^3)$ | $1.685 \times 10^4$ $(2.512 \times 10^3)$ |

[a]Significantly fewer internalized *P. aeruginosa* bacteria in the presence of MAbs specific to the other domains of CFTR, or no MAb at $P < .001$, ANOVA

TABLE 4C

Inhibition of internalization of *P. aeruginosa* strain 324 into transformed human airway epithelial cells (CFT1-LCFSN line) by monoclonal antibodies (MAbs) specific to extracellular domains of CFTR

[mean cfu of *P. aeruginosa* internalized (standard deviation)]

| MAb dilution | C-terminus (MAb CF2) | 4th Outer Domain (MAb CF4) | First Outer Domain (MAb CF3) |
|---|---|---|---|
| 2   | $3.0317 \times 10^4$ $(3.075 \times 10^3)$ | $3.6083 \times 10^4$ $(3.226 \times 10^3)$ | $6.933 \times 10^3$ $(9.91 \times 10^2)^a$ |
| 10  | $3.7317 \times 10^4$ $(3.471 \times 10^3)$ | $4.97 \times 10^4$ $(2.695 \times 10^3)$ | $1.575 \times 10^4$ $(1.5 \times 10^3)^a$ |
| 25  | $3.4433 \times 10^4$ $(3.335 \times 10^3)$ | $3.5633 \times 10^4$ $(2.553 \times 10^3)$ | $3.0767 \times 10^4$ $(2.934 \times 10^3)$ |
| 100 | $3.9167 \times 10^4$ $(2.962 \times 10^3)$ | $3.7067 \times 10^4$ $(3.964 \times 10^3)$ | $3.36 \times 10^4$ $(4.177 \times 10^3)$ |
| 0   | $3.4867 \times 10^4$ $(2.422 \times 10^3)$ | $3.4867 \times 10^4$ $(2.422 \times 10^3)$ | $3.4867 \times 10^4$ $(2.422 \times 10^3)$ |

[a]Significantly fewer internalized *P. aeruginosa* bacteria in the presence of MAbs specific to the other domains of CFTR, or no MAb at $P < .001$, ANOVA To confirm the identification of this domain of CFTR as the binding site for *P. aeruginosa*, peptides corresponding to the first and fourth extracellular domains were synthesized for use in internalization-inhibition assays. Picomole quantities of the synthetic peptide corresponding to the first, not the fourth, predicted extracellular domain of CFTR inhibited epithelial cell internalization of *P. aeruginosa* (Table 5), suggesting that the binding site resides in the first extracellular domain.

TABLE 5

Inhibition of internalization of *P. aeruginosa* strain PAO1 into
transformed human airway epithelial cells (CFT1-LCFSN line) by
synthetic peptides corresponding to the first or fourth predicted
extracellular domains of CFTR
(Mean cfu of *P. aeruginosa* internalized (standard deviation) in
the presence of the synthetic peptide corresponding to the indicated
extracellular domain of CFTR)

| Concentration of inhibitor (nanomoles) | First domain | Fourth domain |
|---|---|---|
| Strain PAO1 | | |
| No inhibitor | $8.17 \times 10^4$ $(2.0861 \times 10^3)$ | |
| 1 | $2.38333 \times 10^4$ $(4.6207 \times 10^3)^a$ | $8.70833 \times 10^4$ $(4.0519 \times 10^3)$ |
| 0.1 | $2.51333 \times 10^4$ $(1.6609 \times 10^3)^a$ | $7.48833 \times 10^4$ $(5.0653 \times 10^3)$ |
| 0.01 | $3.48167 \times 10^4$ $(3.8473 \times 10^3)^a$ | $7.23 \times 10^4$ $(3.6721 \times 10^3)$ |
| 0.001 | $5.53333 \times 10^4$ $(5.2986 \times 10^3)$ | $6.97833 \times 10^4$ $(5.4745 \times 10^3)$ |
| Strain 149 | | |
| No inhibitor | $5.22833 \times 10^4$ $(5.6651 \times 10^3)$ | |
| 1 | $3.7833 \times 10^3$ $(4.491 \times 10^2)^a$ | $5.735 \times 10^4$ $(4.0009 \times 10^3)$ |
| 0.1 | $7.0167 \times 10^3$ $(8.542 \times 10^2)^a$ | $5.52833 \times 10^4$ $(6.0598 \times 10^3)$ |
| 0.01 | $1.705 \times 10^4$ $(2.1333 \times 10^3)^a$ | $4.86 \times 10^4$ $(4.6463 \times 10^3)$ |
| 0.001 | $5.73 \times 10^4$ $(4.006 \times 10^3)$ | $4.75167 \times 10^4$ $(5.9915 \times 10^3)$ |
| Strain 324 | | |
| No inhibitor | $1.467167 \times 10^5$ $(9.4252 \times 10^3)$ | |
| 1 | $1.46167 \times 10^4$ $(2.6955 \times 10^3)^a$ | $1.42 \times 10^5$ $(1.74624 \times 10^4)$ |
| 0.1 | $7.23167 \times 10^4$ $(5.6982 \times 10^3)^a$ | $1.416 \times 10^5$ $(1.19465 \times 10^4)$ |
| 0.01 | $1.405 \times 10^5$ $(9.4323 \times 10^3)$ | $1.412 \times 10^5$ $(7.1986 \times 10^3)$ |
| 0.001 | $1.3938 \times 10^5$ $(7.6735 \times 10^3)$ | $1.3275 \times 10^5$ $(9.408 \times 10^3)$ |

$^a$Significantly fewer internalized *P. aeruginosa* bacteria compared with bacteria inhibited by the fourth extracellular domain peptide at $P < .01$, ANOVA.

In order to verify the above results both the MAb and peptide experiments were repeated using two additional cell lines homozygous for wild-type CFTR, WI-38 diploid human embryonic lung cells and A549 human lung carcinoma cells. The data revealed an identical pattern to that observed using the CFT1-LCFSN cells (Table 6). It is of interest that the amino terminus of CFTR up to amino acid 150, including the first predicted cellular domain, can be deleted from the molecule without affecting its ability to function as a chloride ion channel [17]. Thus CFTR-mediated cellular internalization of *P. aeruginosa* is unrelated to the well-described ion-channel properties of this molecule.

TABLE 6

Inhibition of internalization of *Pseudomonas aeruginosa* strain
PAO1 into transformed human WI-38 cells (diploid embryonic lung
fibroblasts) and A549 cells (lung carcinoma cell line) by monoclonal
antibodies (MAbs) and synthetic peptides specific to the first or
fourth extracellular domains of CFTR
(Mean cfu (standard deviation) of *P. aeruginosa* internalized by
the indicated cell line)

| Inhibitor added to assay | WI 38 cells | A549 cells |
|---|---|---|
| No inhibitor added | $8.4733 \times 10^4$ $(5.111 \times 10^3)$ | $1.00067 \times 10^5$ $(6.088 \times 10^3)$ |
| 1 nM Peptide to 4th Extracellular Domain | $7.3433 \times 10^4$ $(9.124 \times 10^3)$ | $8.7333 \times 10^4$ $(1.1506 \times 10^4)$ |
| 1 nM Peptide of 1st Extracellular Domain | $3.497 \times 10^4$ $(3.751 \times 10^3)^a$ | $3.2833 \times 10^4$ $(4.32 \times 10^3)^a$ |
| MAb to 4th Extracellular Domain | $6.6617 \times 10^4$ $(6.823 \times 10^3)$ | $8.7767 \times 10^4$ $(5.734 \times 10^3)$ |
| MAb to 1st Extracellular Domain | $2.26 \times 10^4$ $(5.166 \times 10^3)^a$ | $1.4833 \times 10^4$ $(4.142 \times 10^3)^a$ |

$^a$Significantly fewer internalized *P. aeruginosa* bacteria compared to corresponding reagent specific to the fourth extracellular domain of CFTR

EXAMPLE 3

The First Extracellular Domain of CFTR Binds to and Inhibits Internalization of *P. aeruginosa* in Mouse Lung Results:

To confirm that binding and internalization of *P. aeruginosa* by the first predicted extracellular domain of CFTR is important in resistance to lung infection, 7-day old Balb/c mice were nasally inoculated with $10^8$ cfu of *P. aeruginosa* stain PAO1 mixed with either 10 nM of the peptide corresponding to the first or fourth predicted extracellular domains of CFTR and the course of bacterial infection was followed for over 24 hours [7, 16]. Twenty-four hours post-infection, mice inoculated with bacteria plus the first extracellular domain peptide had virtually no internalized *P. aeruginosa*, as determined by gentamicin-exclusion assays on single-cell suspensions of lungs (table 7), while mice receiving the bacteria along with the fourth extracellular domain peptide had a median of >$10^4$ cfu of *P. aeruginosa* internalized per mg of lung tissue (Table 7). As a consequence of this inhibition of internalization, mice receiving bacteria plus the first extracellular domain peptide had a median of ~$1.5\times10^5$ cfu of *P. aeruginosa* per mg of lung tissue as compared with a median of ~$2\times10^4$ cfu *P. aeruginosa* per mg of lung tissue for animals infected with bacteria plus the fourth predicted extracellular domain (Table 7). Thus, inhibiting *P. aeruginosa* internalization by blocking the bacterial interaction with CFTR in the lung leads to increased bacterial counts in this tissue, indicating an important mechanism for clearance of *P. aeruginosa* from the lung following inhalation of these organisms.

TABLE 7

Effect of addition of 10 nM of the synthetic peptides corresponding to the first or fourth extracellular domains of CFTR to $10^3$ cfu of *P. aeruginosa* strain PAO1 on internalization by lung cells and total cfu of bacteria in the lungs 24 hours after intranasal infection of 7-day old mice.
(Median cfu (10th–90th percentile cfu) *P. aeruginosa*)

| Peptide added | Internalized per mg. lung tissue | Total per mg. lung tissue |
|---|---|---|
| First extracellular domain | 0 (0–278) | 152,419 (37,860–519,612) |
| Fourth extracellular domain | 13,246 (3,578–49,558) | 20,450 (4,000–61,008) |

EXAMPLE 4

Administration of LPS Core Enhances CFTR Function in ΔF508 Cells Without Inhibiting Ingestion of *P. Aeruginosa*

Results:

Although *P. aeruginosa* LPS core-oligosaccharide has been used in the past in ligand-mediated inhibition of epithelial cell ingestion to demonstrate the importance of this phenomenon in bacterial clearance from the lung [7] and to show that *P. aeruginosa* LPS core-oligosaccharide can inhibit the ingestion, experiments were carried out to determine whether it was possible to deliver the purified bacterial ligand via a route or dose that stimulates CFTR trafficking but is insufficient to inhibit bacterial clearance from the lung. To determine if CFTR trafficking can be stimulated by *P. aeruginosa* complete-core LPS oligosaccharide, an in vitro cellular uptake assay was used. The CTF1 and CFT1-F508 lines of transformed human airway epithelial cells were treated with either *P. aeruginosa* complete- or incomplete-core oligosaccharide for 24 hrs. prior to use of the cells in the standard bacterial uptake assay. Residual extracellular oligosaccharide is washed away prior to adding bacteria for evaluation of uptake. As shown in Table 8, significant stimulation (over 8-fold) of *P. aeruginosa* ingestion by the CFT1 cell line with 3 copies of the mutant ΔF508CFTR-gene (CFT1-F508 cells) was observed by incubating with complete-core oligosaccharide, whereas incomplete-core oligosaccharide resulted in no enhancement in uptake of *P. aeruginosa*. A comparable effect was observed using the parental CFT1 cell line with two copies of the ΔF508-CFTR gene. Therefore, it was found that preincubation with a complete LPS core could enhance the function of ΔF508 CFTR without inhibiting ingestion of *P. aeruginosa*.

TABLE 8

Augmentation of ingestion of *P. aeruginosa* strain PAO1 by treatment of CFT1 or CFT1-F508 cells with complete- or incomplete-core oligosaccharide from *P. aeruginosa* strain PAC557.
[Mean cfu (standard deviation) of *P. aeruginosa* internalized]

| Amount (μg/ml) | Complete core oligosaccharide (CFT1 cells) | Incomplete core oligosaccharide (CFT1-ΔF508) | Complete core oligosaccharide (CFT1-ΔF508) | Incomplete core oligosaccharide (CFT1 cells) |
|---|---|---|---|---|
| 100 | $6.16 \times 10^4$ $(1.15 \times 10^4)^a$ | $7.4 \times 10^3$ $(1.37 \times 10^3)$ | $9.48 \times 10^4$ $(3.84 \times 10^4)^a$ | $8.21 \times 10^3$ $(1.1 \times 10^3)$ |
| 50 | $6.04 \times 10^4$ $(1.47 \times 10^4)^a$ | $7.47 \times 10^3$ $(1.35 \times 10^3)$ | $9.12 \times 10^4$ $(4.59 \times 10^3)^a$ | $1.6 \times 10^4$ $(6.93 \times 10^3)$ |
| 25 | $4.55 \times 10^4$ $(8.27 \times 10^3)^a$ | $1.08 \times 10^4$ $(2.79 \times 10^3)$ | $4.69 \times 10^4$ $(6.64 \times 10^3)^a$ | $1.26 \times 10^4$ $(3.35 \times 10^3)$ |
| 10 | $2.69 \times 10^4$ $(4.4 \times 10^3)$ | $1.69 \times 10^4$ $(3.52 \times 10^3)$ | $2.1 \times 10^4$ $(2.05 \times 10^3)$ | $1.78 \times 10^4$ $(4.82 \times 10^3)$ |
| 1 | $2.53 \times 10^4$ $(5.82 \times 10^3)$ | $2.7 \times 10^4$ $(8.37 \times 10^3)$ | $2.11 \times 10^4$ $(3.72 \times 10^3)$ | $2.78 \times 10^4$ $(5.73 \times 10^3)$ |

[a]Significantly more internalized *P. aeruginosa* bacteria compared to corresponding cell line treated with incomplete core oligosaccharide

EXAMPLE 5

The LPS Core Enhances CFTR Function in vivo by Enhancing Cellular Uptake and P. aeruginosa For the above in vitro finding to be of potential therapeutic value there was a need to demonstrate that treatment of an animal with the bacterial ligand for ingestion stimulates P. aeruginosa uptake in vivo and promotes bacterial clearance from the lung. The experimental approach used was quite different from that used to generate previously reported data [7] where it was shown that inclusion of the complete-core oligosaccharide ligand in the bacterial inoculum inhibited P. aeruginosa ingestion and promoted enhanced bacterial growth in the lungs of neonatal mice. The in vitro results (Table 8) suggest that purified ligand (a small molecular sized, nonimmunogenic carbohydrate) stimulates receptor trafficking and enhances P. aeruginosa uptake if cells are exposed to it prior to exposure to the bacterial inoculum. Treating an individual with purifides and could potentially enhance expressed of the bacterial receptor that promotes epithelial cell ingestion, leading to greater clearance of bacteria in vivo. This was initially evaluated in mice by priming them with purified oligosaccharide 24 hrs. prior to bacterial challenge, using the model of Tang et al. [16].

To avoid any inhibitory effects of complete-core oligosaccharide on bacterial clearance, the oligosaccharide was administered intraperitoneally (IP) and bacterial clearance following lung challenge was monitored. Although it is recognized that clearance occurs by cellular binding of bacteria in the lumen of the airway, and it is also clearly recognized that CFTR, the ligand for P. aeruginosa ingestion, is located in the apical membrane, the initial experiments were performed using systemic therapy. It was reasoned that if enhanced bacterial uptake and clearance were obtained using this route, potential inhibitory complications from complete-core oligosaccharide in the airway lumen could be minimized. As shown in Table 9, IP injection of 100 μg of P. aeruginosa complete-core oligosaccharide resulted in significantly reduced levels of bacteria in the airways of neonatal mice 24 hrs. after nasal application of $5 \times 10^7$ cfu of P. aeruginosa strain PAO1, as compared to mice primed with incomplete-core LPS oligosaccharide. In addition to measuring the bacterial load in the lungs, histopathologic examination of lungs of these mice showed that those receiving the complete-core oligosaccharide primer had only mildly affected tissues, whereas the incomplete-core oligosaccharide primed mice had extensive inflammation and damage, identical to that reported by Tang et al. [16] in mice infected for 24 hours by P. aeruginosa PAO1.

TABLE 9

Bacterial load in lungs of neonatal mice (24 hrs. after challenge) primed 24 hrs. prior to challenge with P. aeruginosa LPS-core oligosaccharides.

| Geometric mean cfu bacteria/lung (95% C.I.) in mice primed with P. aeruginosa complete-core LPS oligosaccharide 24 hrs. prior to bacterial challenge | Geometric mean cfu bacteria/lung (95% C.I.) in mice primed with P. aeruginosa incomplete-core LPS oligosaccharide 24 hrs. prior to bacterial challenge |
|---|---|
| 1,980 (618–5353) | 58,529 (19,593–153,945) |

The mechanism by which the LPS core causes enhanced clearance of bacteria from the lungs is unknown. Possibly it stimulates production of an apical-membrane receptor for bacterial ingestion, like CFTR. Small amounts of oligosaccharide may get to the luminal surface via systemic transfer where they may bind to the epithelial for and stimulate production of more receptor, or there may be a way that adsorption of oligosaccharide from the basal side of the epithelial cells also stimulates receptor production. Alternately, several studies have suggested an intracellular function for CFTR [19–21] and other studies have demonstrated the presence of CFTR in endosomes [22] and clathrin-coated vesicles [23]. Thus, it is possible that entry of P. aeruginosa oligosaccharide from the basal side of the cell stimulates intracellular CFTR (or another membrane protein involved in internalization of P. aeruginosa) trafficking by binding to the intracellular CFTR (or other receptor).

Additional validation of these results was sought by repeating the experiment of priming mice with oligosaccharide injected IP 24 hours prior to nasal application of P. aeruginosa, but this time measuring bacterial uptake by the lung epithelial cells 4 hours after infection, using the gentamicin-survival assay. In this study mice primed with complete-core oligosaccharide has 3 to 4 times as many intracellular P. aeruginosa cells (mean 280,870±30,180) compared to mice primed with either nothing (82,200±2,660) or incomplete-core oligosaccharide (67,980±4790) ($P<0.001$, ANOVA). Four-hours post infection mice primed with complete-core oligosaccharide had slightly (nonsignificant) lower total cfu per lung. Thus, as opposed to the results shown in FIG. 4 of reference [7], where inclusion of the complete-core oligosaccharide with the bacterial inoculum inhibited cellular ingestion and promoted P. aeruginosa survival in the lungs of neonatal mice, priming mice with the same material 24 hours prior to infection stimulated bacterial uptake and clearance from the lungs, suggesting that epithelial-cell receptors had been upregulated by the priming.

In conclusion, published results identified [7] the complete outer-core oligosaccharide portion of the P. aeruginosa lipopolysaccharide (LPS) as the bacterial ligand for internalization by human airway cells. Results here identify the first predicted extracellular domain of CFTR, encompassing amino acids 103–117 of the mature protein, as the cellular receptor, and this receptor can be up-regulated by pretreatment of either cells or animals with complete core-oligosaccharide derived from the P. aeruginosa LPS.

Reference

1. Welsh M J, Anderson M P, Rich D P, Berger H A, Sheppard D N. "The CFTR chloride channel." *Chloride Channels*. Ed. Guggino W B. Current Topics in Membranes. San Diego: Academic Press, Inc. 42: 153–171, 1994.
2. Smith J J, Travis S M, Greenberg E P, Welsh M J. Cystic fibrosis airway epithelia fail to kill bacteria because of abnormal airway surface fluid. Cell. 85:229–236; 1996.
3. Cystic Fibrosis Foundation. Patient registry 1994 annual data report, Bethesda, Md. 1995.
4. Huang N N, Schidlow D V, Szatrowski T H, Palmer J, Laraya-Cuasay L R, Yeung W, Hardy K, Quitell L, Fiel S. Clinical features, survival rate and prognostic factors in young adults with cystic fibrosis. Am J Med. 82:871–879; 1987.
5. Pedersen S S, Kharazmi A, Espersen F, Hoiby N. P. aeruginosa alginate in cystic fibrosis sputum and the inflammatory response. Infect Immun. 58:3363–3368; 1990.
6. Demko C A, Byard P J, Davis P B. Gender differences in cystic fibrosis: P. aeruginosa infection. J Clin Epidemiol. 48:1041–1049; 1995.

7. Pier G B, Grout M, Zaidi T S, Olsen J C, Johnson L G, Yankaskas J R, Goldberg J B. Role of mutant CFTR in hypersusceptibility of cystic fibrosis patients to lung infections. Science. 271:64–67; 1996.
8. Olsen J C, Johnson L G, Stutts M J, SArkadi B, Yankas J R, Swanstrom R, Boucher R C. Correction of the apical membrane chloride permeability defect in polarized cystic fibrosis airway epithelia following retroviral-mediated gene transfer. Hum Gene Ther. 3:253–266; 1992.
9. Sarkadi B, Bauzon D, Huckle W R, Earp H S, Berry A, Suchindran H, Price E M, Olsen J C, Boucher R C, Scarborough G A. Biochemical characterization of the cystic fibrosis transmembrane conductance regulator in normal and cystic fibrosis epithelial cells. J. Biol. Chem. 267:2087–95; 1992.
10. Cheng S H, Fang S L, Zabner J, Marshall J, Piraino S, Schiavi SC, Jefferson D M, Welsh M J, Smith A E. Functional activation of the cystic fibrosis trafficking mutant delta F508-CFTR by overexpression. Amer J Physiol-Lung Cell M Ph. 12:L615–L624; 1995.
11. O'Riordan C R, Erickson A, Bear C, Li C H, Manavalan P, Wang K X, Marshall J, Scheule R K, Mcpherson J M, Cheng S H, et al. Purification and characterization of recombinant cystic fibrosis transmembrane conductance regulator from Chinese hamster ovary and insect cells. J Biol Chem. 270:17033–17043; 1995.
12. Walker J, Watson J, Holmes C, Edelman A, Banting G. Production and characterization of monoclonal and polyclonal antibodies to different regions of the cystic fibrosis transmembrane conductance regulator (CFTR): detection of immunologically related proteins. J Cell Sci. 108:2433–2444; 1995.
13. Fleiszig S M J, Zaidi T S, Pier G B. *P. aeruginosa* invasion of and multiplication within corneal epithelial cells in vitro. Infect Immun. 63:4072–4077; 1995.
14. Rosner B. "Analysis of variance." *Fundamentals of Biostatistics*. Boston, Mass.: Duxbury Press 498–503, 1990.
15. Coyne M J, Russell K S, Coyle C L, Goldberg J B. The *P. aeruginosa* algC gene encodes phosphoglucomutase, required for the synthesis of a complete lipopolysaccharide core. J Bacteriol. 176:3500–3507; 1994.
16. Tang H, Kays M, Prince A Role of *P. aeruginosa* pili in acute pulmonary infection. Infect Immun. 63:1278–1285; 1995.
17. Carroll T P, Morales M M, Fulmer S B, Allen S S, Flotte T R, Cutting G R, Guggino W B. Alternate translation initiation codons can create functional forms of cystic fibrosis transmembrane conductance regulator. J Biol Chem. 270:119–416; 1995.
18. Prince L S, Workman R B, Jr., Marchase R B. Rapid endocytosis of the cystic fibrosis transmembrane conductance regulator chloride channel. Proc Natl Acad Sci USA. 91:5192–6; 1994.
19. Barasch J, Kiss B, Prince A, Saiman L, Gruenert D, al-Awqati Q. Defective acidification of intracellular organelles in cystic fibrosis. Nature. 352:70–3; 1991.
20. al-Awqati Q, Barasch J, Landry D. Chloride channels of intracellular organelles and their potential role in cystic fibrosis. J Exp Biol. 172:24566; 1992.
21. Barasch J, Alawqati Q. Defective acidification of the biosynthetic pathway in cystic fibrosis. J Cell Sci. 229–233; 1993.
22. Webster P, Vanacore L, Nairn A C, Marino C R. Subcellular localization of CFTR to endosomes in a ductal epithelium. Am J Physiol. 267:C340–8; 1994.
23. Bradbury N A, Cohn J A, Venglarik C J, Bridges R J. Biochemical and biophysical identification of cystic fibrosis transmembrane conductance regulator chloride channels as components of endocytic clathrin-coated vesicles. J Biol Chem. 269:8296–8302; 1994.

Each of the foregoing patents, patent applications and references is herein incorporated by reference in its entirety. Having described the presently preferred embodiments, in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

What I claim is:

1. A pharmaceutical preparation comprising a CFTR expression regulator, wherein the CFTR expression regulator is free of lipid A and is a polysaccharide that is an LPS core moiety comprising

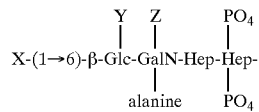

wherein X is selected from the group consisting of glucose, glucose-rhamnose and H;

wherein Y is selected from the group consisting of rhamnose and H; and wherein Z is selected from the group consisting of glucose and H; and a pharmaceutically acceptable carrier.

2. The pharmaceutical preparation of claim 1 wherein the polysaccharide comprises

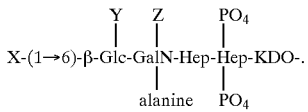

3. A pharmaceutical preparation comprising a CFTR expression regulator, wherein the CFTR expression regulator is free of lipid A and is a polysaccharide that is an LPS core moiety comprising

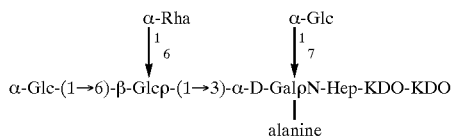

wherein X is selected from the group consisting of glucose, glucose-rhamnose and H;

wherein Y is selected from the group consisting of rhamnose and H; and wherein Z is selected from the group consisting of glucose and H; and a pharmaceutically acceptable carrier.

4. A pharmaceutical preparation comprising a CFTR expression regulator, wherein the CFTR expression regulator is free of lipid A and is a polysaccharide that is an LPS core moiety comprising

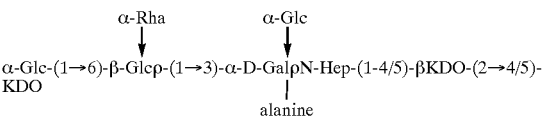

wherein X is selected from the group consisting of glucose, glucose-rhamnose and H;

wherein Y is selected from the group consisting of rhamnose and H; and wherein Z is selected from the group consisting of glucose and H; and a pharmaceutically acceptable carrier.

5. A pharmaceutical preparation comprising a CFTR expression regulator, wherein the CFTR expression regulator is free of lipid A and is a polysaccharide that is an LPS core moiety comprising

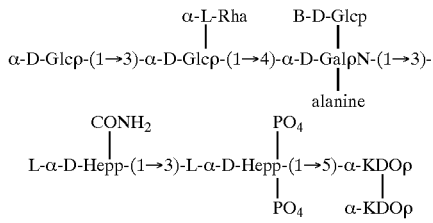

wherein X is selected from the group consisting of glucose, glucose-rhamnose and H;

wherein Y is selected from the group consisting of rhamnose and H; and wherein Z is selected from the group consisting of glucose and H; and a pharmaceutically acceptable carrier.

6. The pharmaceutical preparation of claim 1 wherein the polysaccharide comprises a CFTR binding fragment of a lipopolysaccharide of *Pseudomonas aeruginosa*.

7. The pharmaceutical preparation of claim 1 wherein the pharmaceutical preparation is sterile.

8. The pharmaceutical preparation of claim 1 wherein the pharmaceutical preparation is formulated in a unit dosage in an amount effective for treating Pseudomal infection.

9. The pharmaceutical preparation of claim 1 wherein the pharmaceutical preparation is formulated as an aerosol for inhalation.

10. The pharmaceutical preparation of claim 1 wherein the pharmaceutical preparation is formulated as an injectable preparation.

11. A composition of matter comprising a covalent conjugate of a non-toxic lipid for associating a bioactive agent with a polysaccharide, wherein the non-toxic lipid is not lipid A and a polysaccharide comprising

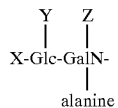

wherein X is selected from the group consisting of glucose, glucose-rhamnose and H; Y is selected from the group consisting of rhamnose and H; and Z is selected from the group consisting of glucose and H.

12. The composition of matter of claim 11 wherein the polysaccharide comprises

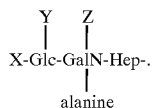

13. The composition of matter of claim 11 wherein the polysaccharide comprises

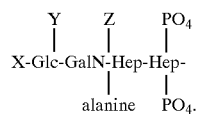

14. The composition of matter of claim 11 wherein the polysaccharide comprises

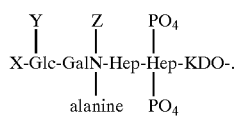

15. The composition of matter of claim 11 wherein the polysaccharide comprises

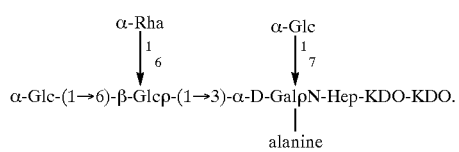

16. The composition of matter of claim 11 wherein the polysaccharide comprises

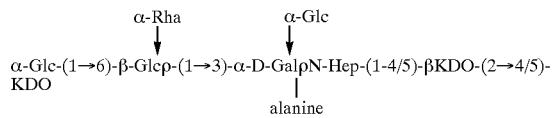

17. The composition of matter of claim 11 wherein the polysaccharide comprises

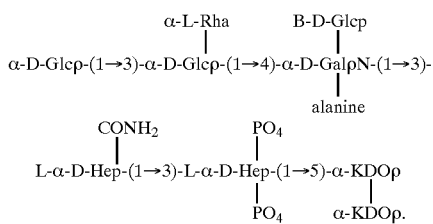

18. The composition of matter of claim 11 wherein the polysaccharide comprises a CFTR binding fragment of a lipopolysaccharide of *Pseudomonas aeruginosa.*

19. The composition of matter of claim 11 wherein the lipid has the following structural formula: $CH_3(CH_2)_nCOOH$ wherein $n=1$–$50$.

20. The composition of matter of claim 19 wherein the lipid is in the wall of a liposome containing a bioactive agent.

21. A composition of matter comprising a covalent conjugate of a bioactive agent wherein the bioactive agent is not lipid A and a polysaccharide comprising

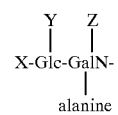

wherein X is selected from the group consisting of glucose, glucose-rhamnose and H; Y is selected from the group consisting of rhamnose and H; and Z is selected from the group consisting of glucose and H.

22. The composition of matter of claim 21 wherein the polysaccharide comprises

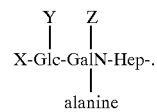

23. The composition of matter of claim 21 wherein the polysaccharide comprises

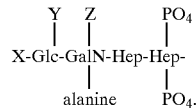

24. The composition of matter of claim 21 wherein the polysaccharide comprises

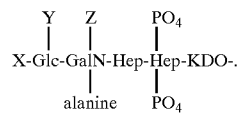

25. The composition of matter of claim 21 wherein the polysaccharide comprises

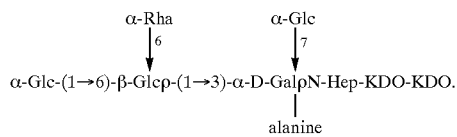

26. The composition of matter of claim 21 wherein the polysaccharide comprises

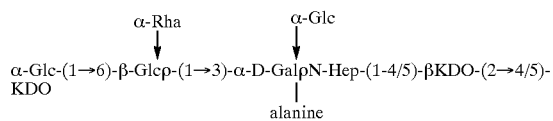

27. The composition of matter of claim 21 wherein the polysaccharide comprises

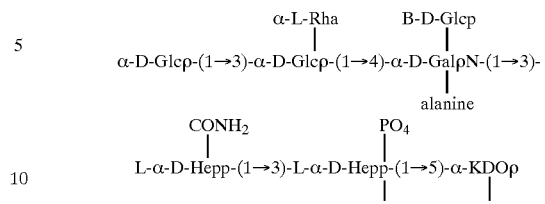

28. The composition of matter of claim 21 wherein the polysaccharide comprises a CFTR binding fragment of a lipopolysaccharide of *Pseudomonas aeruginosa*.

* * * * *